US008034560B2

(12) United States Patent
Croce

(10) Patent No.: US 8,034,560 B2
(45) Date of Patent: Oct. 11, 2011

(54) MICRORNA-BASED METHODS AND COMPOSITIONS FOR THE DIAGNOSIS, PROGNOSIS AND TREATMENT OF ACUTE MYELOID LEUKEMIA (AML)

(75) Inventor: Carlo M. Croce, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 12/523,915

(22) PCT Filed: Jan. 29, 2008

(86) PCT No.: PCT/US2008/001157
§ 371 (c)(1),
(2), (4) Date: Aug. 21, 2009

(87) PCT Pub. No.: WO2008/094545
PCT Pub. Date: Aug. 7, 2008

(65) Prior Publication Data

US 2010/0048681 A1 Feb. 25, 2010

Related U.S. Application Data

(60) Provisional application No. 60/898,578, filed on Jan. 31, 2007.

(51) Int. Cl.
*C12Q 1/68* (2006.01)

(52) U.S. Cl. .......................................................... 435/6

(58) Field of Classification Search ....................... 435/6
See application file for complete search history.

(56) References Cited

U.S. PATENT DOCUMENTS 4,172,124 A 10/1979 Koprowski et al.
4,196,265 A 4/1980 Koprowski et al.
4,608,337 A 8/1986 Croce
4,693,975 A 9/1987 Kozbor et al.
4,701,409 A 10/1987 Croce
5,015,568 A 5/1991 Tsujimoto et al.
5,149,628 A 9/1992 Croce
5,198,338 A 3/1993 Croce
5,202,429 A 4/1993 Tsujimoto et al.
5,459,251 A 10/1995 Tsujimoto et al.
5,506,106 A 4/1996 Croce et al.
5,506,344 A 4/1996 Tsujimoto et al.
5,523,393 A 6/1996 Tsujimoto et al.
5,567,586 A 10/1996 Croce
5,595,869 A 1/1997 Tsujimoto et al.
5,633,135 A 5/1997 Croce et al.
5,633,136 A 5/1997 Croce et al.
5,674,682 A 10/1997 Croce et al.
5,688,649 A 11/1997 Croce et al.
5,695,944 A 12/1997 Croce et al.
5,928,884 A 7/1999 Croce et al.
5,939,258 A 8/1999 Croce et al.
5,985,598 A 11/1999 Russo et al.
6,040,140 A 3/2000 Croce et al.
6,130,201 A 10/2000 Croce et al.
6,242,212 B1 6/2001 Croce et al.
6,255,293 B1 7/2001 Kimchi
6,258,541 B1 7/2001 Chapkin et al.
6,774,217 B1 8/2004 Croce et al.
6,924,414 B2 8/2005 Croce et al.
7,060,811 B2 6/2006 Aldaz et al.
7,141,417 B1 11/2006 Croce et al.
7,175,995 B1 2/2007 Russo et al.
7,217,568 B2 5/2007 Jamieson et al.
7,220,834 B2 5/2007 Croce et al.
7,232,806 B2 6/2007 Tuschl et al.
7,390,792 B2 6/2008 Srivastava et al.
7,585,969 B2 9/2009 Stoffel et al.
7,592,441 B2 9/2009 Bentwich et al.
7,618,814 B2 11/2009 Bentwich et al.
7,642,348 B2 1/2010 Bentwich et al.
7,667,090 B2 2/2010 Croce
7,670,840 B2 3/2010 Croce et al.
7,709,616 B2 5/2010 Bentwich et al.
7,723,030 B2 5/2010 Croce et al.
7,723,035 B2 5/2010 Croce et al.
7,728,189 B2 6/2010 Croce
7,749,715 B2 7/2010 Russo et al.
7,777,005 B2 8/2010 Croce et al.
2001/0026796 A1 10/2001 Croce et al.
2002/0086331 A1 7/2002 Croce et al.
2002/0116726 A1 8/2002 Croce et al.
2004/0033502 A1 2/2004 Williams et al.
2004/0078834 A1 4/2004 Croce (Continued)

FOREIGN PATENT DOCUMENTS

WO 90/15156 12/1990

(Continued)

OTHER PUBLICATIONS

Garzon et al. Blood, (Nov. 16, 2006) vol. 108, No. 11, Part 1, pp. 49A, abstract #151. Meeting Info.: 48th Annual Meeting of the American-Society-of-Hematology. Orlando, FL, USA. Dec. 9-12, 2006.*

Saiz et al. Univ Toronto, Inst Med Sci, Toronto, ON M5S 1A1, CanadaBlood, (Nov. 16, 2004) vol. 104, No. 11, Part 1, pp. 320A. Meeting Info.: 46th Annual Meeting of the American-Society-of-Hematology. San Diego, CA, USA. Dec. 4-7, 2004. Amer Soc Hemato.*

Akahoshi, M. et al., "Myeloproliferative Disorders Terminating in Acute Megakaryoblastic Leukemia with Chromosome 3q26 Abnormality," Cancer, 1987, pp. 2654-2661, vol. 60.

Akao, Y. et al., "let-7 MicroRNA Functions as a Potential Growth Suppressor in Human Colon Cancer Cells," Biol. Pharm. Bull., May 2006, pp. 903-906, vol. 29, No. 5.

Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.

Aqeilan, R. I. et al., "Targeted Deletion of WWOX Reveals a Tumor Suppressor Function," PNAS, Mar. 2007, pp. 3949-3954, vol. 104, No. 10.

Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.

(Continued)

*Primary Examiner* — Brian Whiteman

(74) *Attorney, Agent, or Firm* — MacMillan, Sobanski & Todd, LLC

(57) ABSTRACT

The present invention provides novel methods and compositions for the diagnosis, prognosis and treatment of acute myeloid leukemia (AML). The invention also provides methods of identifying anti-AML agents.

7 Claims, 25 Drawing Sheets

U.S. PATENT DOCUMENTS

2004/0152112 A1 8/2004 Croce et al.
2004/0265316 A1 12/2004 Croce et al.
2004/0265930 A1 12/2004 Sun et al.
2005/0019890 A1 1/2005 Croce
2005/0059005 A1 3/2005 Tuschl et al.
2005/0069918 A1 3/2005 Claret
2005/0074797 A1 4/2005 Croce et al.
2005/0112630 A1 5/2005 Shaughnessy et al.
2005/0176025 A1 8/2005 McSwiggen et al.
2005/0181385 A1 8/2005 Linsley et al.
2005/0186589 A1 8/2005 Kowalik et al.
2005/0256072 A1 11/2005 Aronin et al.
2005/0260639 A1 11/2005 Nakamura et al.
2005/0266443 A1 12/2005 Croce et al.
2005/0287530 A1 12/2005 Croce et al.
2006/0019286 A1 1/2006 Horvitz et al.
2006/0024780 A1 2/2006 Aldaz et al.
2006/0037088 A1 2/2006 Li
2006/0075511 A1 4/2006 Croce et al.
2006/0084059 A1 4/2006 Yip et al.
2006/0099619 A1 5/2006 Remacle et al.
2006/0105340 A1 5/2006 Croce et al.
2006/0105360 A1* 5/2006 Croce et al. ...................... 435/6
2006/0127895 A1 6/2006 Sabapathy
2006/0165659 A1 7/2006 Croce et al.
2006/0166918 A1 7/2006 Heidenreich et al.
2006/0185027 A1 8/2006 Bartel et al.
2006/0188924 A1 8/2006 Russo et al.
2006/0188959 A1 8/2006 Croce et al.
2006/0189557 A1 8/2006 Slack et al.
2006/0247448 A1 11/2006 Boivin et al.
2006/0292616 A1 12/2006 Neely et al.
2007/0050146 A1 3/2007 Bentwich et al.
2007/0054849 A1 3/2007 Nakamura et al.
2007/0065840 A1 3/2007 Naguibneva et al.
2007/0065844 A1 3/2007 Golub et al.
2007/0072230 A1 3/2007 Croce et al.
2007/0099196 A1 5/2007 Kauppinen et al.
2007/0123482 A1 5/2007 Stoffel et al.
2007/0161004 A1 7/2007 Brown et al.
2007/0178105 A1 8/2007 Croce et al.
2007/0178502 A1 8/2007 Reed
2007/0212727 A1 9/2007 Szalay et al.
2007/0213292 A1 9/2007 Stoffel et al.
2007/0292878 A1 12/2007 Raymond
2008/0026951 A1 1/2008 Brown et al.
2008/0050744 A1 2/2008 Brown et al.
2008/0171667 A1 7/2008 Brown et al.
2008/0176766 A1 7/2008 Brown et al.
2008/0182245 A1 7/2008 Brown et al.
2008/0193943 A1 8/2008 Murray
2008/0254473 A1 10/2008 Chen et al.
2008/0256650 A1 10/2008 Croce
2008/0261908 A1 10/2008 Croce et al.
2008/0306006 A1 12/2008 Croce et al.
2008/0306017 A1 12/2008 Croce et al.
2008/0306018 A1 12/2008 Croce et al.
2009/0005336 A1 1/2009 Wang
2009/0023594 A1 1/2009 Mouritzen et al.
2009/0029932 A1 1/2009 Voinnet et al.
2009/0061424 A1 3/2009 Chen
2009/0092974 A1 4/2009 Davison et al.
2009/0099034 A1 4/2009 Ahlquist et al.
2009/0123533 A1 5/2009 Croce et al.
2009/0123912 A1 5/2009 Raymond
2009/0123933 A1 5/2009 Mishra
2009/0131348 A1 5/2009 Labourier et al.
2009/0131354 A1 5/2009 Bader et al.
2009/0131356 A1 5/2009 Bader et al.
2009/0163430 A1 6/2009 Johnson et al.
2009/0163434 A1 6/2009 Bader et al.
2009/0163435 A1 6/2009 Bader et al.
2009/0175827 A1 7/2009 Byrom et al.
2009/0176723 A1 7/2009 Brown et al.
2009/0192102 A1 7/2009 Bader et al.
2009/0192111 A1 7/2009 Bader et al.
2009/0192114 A1 7/2009 Ovcharenko et al.
2009/0209450 A1 8/2009 Croce et al.
2009/0222934 A1 9/2009 Croce
2009/0227533 A1 9/2009 Bader et al.
2009/0232893 A1 9/2009 Bader et al.
2009/0253780 A1 10/2009 Takeshita et al.
2009/0263803 A1 10/2009 Beaudenon et al.
2009/0270484 A1 10/2009 Croce et al.
2009/0281167 A1 11/2009 Shen et al.
2009/0306194 A1 12/2009 Ford et al.
2010/0004322 A1 1/2010 Croce
2010/0048681 A1 2/2010 Croce
2010/0120898 A1 5/2010 Croce et al.
2010/0137410 A1 6/2010 Croce
2010/0144850 A1 6/2010 Croce
2010/0173319 A1 7/2010 Croce et al.
2010/0184032 A1 7/2010 Georgantas et al.
2010/0184830 A1 7/2010 Croce et al.
2010/0184842 A1 7/2010 Croce
2010/0192235 A1 7/2010 Croce
2010/0197770 A1 8/2010 Wang et al.
2010/0197774 A1 8/2010 Croce et al.
2010/0203544 A1 8/2010 Croce et al.
2010/0234241 A1 9/2010 Croce et al.
2010/0249213 A1 9/2010 Croce
2010/0257618 A1 10/2010 Croce et al.

FOREIGN PATENT DOCUMENTS

WO 91/00364 1/1991
WO 91/07424 5/1991
WO 93/12136 6/1993
WO 94/10343 5/1994
WO 94/24308 10/1994
WO 94/26930 11/1994
WO 96/13514 5/1996
WO 96/35124 11/1996
WO 97/29119 8/1997
WO 98/09510 3/1998
WO 00/03685 1/2000
WO 00/50565 8/2000
WO 00/55169 9/2000
WO 01/44466 6/2001
WO 01/68666 9/2001
WO 01/77343 10/2001
WO 01/87958 11/2001
WO 02/064171 8/2002
WO 02/064172 8/2002
WO 03/029459 4/2003
WO 03/078662 9/2003
WO 03/092370 11/2003
WO 2004/033659 4/2004
WO 2004/043387 5/2004
WO 2004/079013 9/2004
WO 2004/098377 11/2004
WO 2005/017711 2/2005
WO 2005/020795 3/2005
WO 2005/078139 8/2005
WO 2005/080601 9/2005
WO 2005/118806 12/2005
WO 2006/105486 10/2006
WO 2006/108718 10/2006
WO 2006/119266 11/2006
WO 2006/133022 12/2006
WO 2006/137941 12/2006
WO 2007/016548 2/2007
WO 2007/033023 3/2007
WO 2007/044413 4/2007
WO 2007/081680 7/2007
WO 2007/081720 7/2007
WO 2007/081740 7/2007
WO 2007/084486 7/2007
WO 2007/109236 9/2007
WO 2007/127190 11/2007
WO 2008/008430 1/2008
WO 2008/036776 3/2008
WO 2008/054828 5/2008
WO 2008/054828 C 5/2008
WO 2008/070082 6/2008
WO 2008/073920 6/2008
WO 2008/094545 8/2008
WO 2008/097277 8/2008

| | | |
|---|---|---|
| WO | 2008/136971 | 11/2008 |
| WO | 2008/153987 | 12/2008 |
| WO | 2008/157319 | 12/2008 |
| WO | 2009/018303 | 2/2009 |
| WO | 2009/020905 | 2/2009 |
| WO | 2009/026487 | 2/2009 |
| WO | 2009/033140 | 3/2009 |
| WO | 2009/049129 | 4/2009 |
| WO | 2009/055773 | 4/2009 |
| WO | 2009/064590 | 5/2009 |
| WO | 2009/070653 | 6/2009 |
| WO | 2009/100029 | 8/2009 |
| WO | 2009/108853 | 9/2009 |
| WO | 2009/108856 | 9/2009 |
| WO | 2009/108860 | 9/2009 |
| WO | 2009/108866 | 9/2009 |
| WO | 2009/152300 | 12/2009 |
| WO | 2010/019694 | 2/2010 |
| WO | 2010/059779 | 5/2010 |
| WO | 2010/065156 | 6/2010 |
| WO | 2010/099161 | 9/2010 |

OTHER PUBLICATIONS

Bartel, D. P., "MicroRNAs: Target Recognition and Regulatory Functions," Cell, Jan. 2009, pp. 215-233, vol. 136.
Bednarek, A. K. et al., "WWOX, the FRA16D Gene, Behaves as a Suppressor of Tumor Growth," Cancer Research, Nov. 2001, pp. 8068-8073, vol. 61.
Bejenaro, etal., "Ultraconserved Elements in the Human Genome," Electronic Suppl. Data, Science, 2004.
Bejerano, G. et al., "Ultraconserved Elements in the Human Genome," Science, May 2004, pp. 1321-1325, vol. 304.
Bell, D. A., "Origins and Molecular Pathology of Ovarian Cancer," Modern Pathology, 2005, pp. S19-S32, vol. 18.
Bichi, R. et al., "Human Chronic Lymphocytic Leukemia Modeled in Mouse by Targeted TCL1 Expression," PNAS, May 2002, pp. 6955-6960, vol. 99, No. 10.
Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.
Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.
Budhu, A. et al., "Identification of Metastasis-Related MicroRNAs in Hepatocellular Carcinoma," Hepatology, Mar. 2008, pp. 897-907, vol. 47, No. 3.
Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.
Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.
Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.
Calin, G. A. et al., "Human MicroRNA Genes are Frequently Located at Fragile Sites and Genomic Regions Involved in Cancers," PNAS, Mar. 2004, pp. 2999-3004, vol. 101, No. 9.
Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.
Calin, G. A. et al., "MicroRNA Signatures in Human Cancers," Nature Reviews Cancer, Nov. 2006, pp. 857-866, vol. 6.
Calin, G. A. et al., "MiR-15a and MiR-16-1 Cluster Functions in Human Leukemia," PNAS, Apr. 2008, pp. 5166-5171, vol. 105, No. 13.
Calin, G. A. et al., "Ultraconserved Regions Encoding ncRNAs are Altered in Human Leukemias and Carcinomas," Cancer Cell, Sep. 2007, pp. 215-229, vol. 12.
Chan, J. A. et al., "MicroRNA-21 is an Antiapoptotic Factor in Human Glioblastoma Cells," Cancer Research, Jul. 2005, pp. 6029-6033, vol. 65, No. 14.
Chang, N.-S. et al., "Molecular Mechanisms Underlying WOX1 Activation During Apoptotic and Stress Responses," Biochemical Pharmacology, 2003, pp. 1347-1354, vol. 66.
Chang, T.-C. et al., "Widespread MicroRNA Repression by Myc Contributes to Tumorigenesis," Nat Genet., Jan. 2008, pp. 43-50, vol. 40, No. 1.
Chen, C.-Z. et al., "MicroRNAs as Regulators of Mammalian Hematopoiesis," Seminars in Immunology, 2005, pp. 155-165, vol. 17.
Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.
Ciafre, S. A. et al., "Extensive Modulation of a Set of MicroRNAs in Primary Glioblastoma," Biochemical and Biophysical Research Communications, 2005, pp. 1351-1358, vol. 334.
Cimmino, A. et al., "miR-15 and miR-16 Induce Apoptosis by Targeting BCL2," PNAS, Sep. 2005, pp. 13944-13949, vol. 102, No. 39.
Cimmino, A. et al., Corrections to "miR-15 and miR-16 Induce Apoptosis by Targeting BCL2," PNAS, Feb. 2006, pp. 2464-2465, vol. 103, No. 7.
Costinean, S. et al., "Pre-B Cell Proliferation and Lymphoblastic Leukemia/ High-Grade Lymphoma in Eμ-miR155 Transgenic Mice," PNAS, May 2006, pp. 7024-7029, vol. 103, No. 18.
Croce, C. M. et al., "miRNAs, Cancer, and Stem Cell Division," Cell, 2005, pp. 6-7, vol. 36.
Croce, C. M. et al., "Role of FHIT in Human Cancer," Journal of Clinical Oncology, May 1999, pp. 1618-1624, vol. 17, No. 5.
Croce, C. M., "Causes and Consequences of MicroRNA Dysregulation in Cancer," Nature Reviews Genetics, Oct. 2009, pp. 704-714, vol. 10.
Croce, C. M., "Oncogenes and Cancer," The New England Journal of Medicine, Jan. 2008, pp. 502-511, vol. 358, No. 5.
Dalmay, T. et al., "MicroRNAs and the Hallmarks of Cancer," Oncogene, 2006, pp. 6170-6175, vol. 25.
Davies, F. E. et al., "Insights into the Multistep Transformation of MGUS to Myeloma Using Microarray Expression Analysis," Blood, Dec. 2003, pp. 4504-4511, vol. 102, No. 13.
Dohner, H. et al., "Genomic Aberrations and Survival in Chronic Lymphocytic Leukemia," The New England Journal of Medicine, Dec. 2000, pp. 1910-1916, vol. 343, No. 26.
Druck, etal., "FHIT," Atlas of Genetics and Cytogenetics in Oncology and Haematology, 2007, pp. 171-178, vol. 2.
Eis, P. S. et al., "Accumulation of miR-155 and BIC RNA in Human B Cell Lymphomas," PNAS, Mar. 2005, pp. 3627-3632, vol. 102, No. 10.
European Patent Application, EP 1795203 A2, Croce et al., Application No. 06010581.4, filed Feb. 7, 1997, published Jun. 13, 2007.
European Search Report, Application No. 06800599.0 dated Oct. 19, 2009.
European Search Report, Application No. 06814375.9 dated Oct. 8, 2009.
European Search Report, Application No. 06825457.2 dated Sep. 16, 2009.
European Search Report, Application No. 07716208.9 dated Nov. 10, 2009.
European Search Report, Application No. 07717734.3 dated Nov. 9, 2009.
European Search Report, Application No. 07717903.4 dated Oct. 23, 2009.
European Search Report, Application No. 07753450.1 dated Jan. 12, 2009.
European Search Report, Application No. 07810382.7 dated Sep. 14, 2009.
European Search Report, Application No. 07867402.5 dated Mar. 16, 2010.
European Search Report, Application No. 07872618.9 dated Jul. 5, 2010.
European Search Report, Application No. 08767439.6 dated May 12, 2010.
European Search Report, Application No. 08768266.2 dated Jul. 1, 2010.

European Search Report, Application No. 08796821.0 dated Aug. 4, 2010.
European Search Report, Application No. 08841700.1 dated Jun. 2, 2010.
Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.
Fabbri, M. et al., "MicroRNAs," The Cancer Journal, Jan./Feb. 2008, pp. 1-6, vol. 14, No. 1.
Fabbri, M. et al., "WWOX Gene Restoration Prevents Lung Cancer Growth in Vitro and in Vivo," PNAS, Oct. 2005, pp. 15611-15616, vol. 102, No. 43.
Fong, Y. et al., "Muir-Torre-Like Syndrome in FHIT-Deficient Mice," PNAS, Apr. 2000, pp. 4742-4747, vol. 97, No. 9.
Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.
Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.
Garzon, R. et al., "MicroRNA Fingerprints During Human Megakaryocytopoiesis," PNAS, Mar. 2006, pp. 5078-5083, vol. 103, No. 13.
Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.
Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.
Gourley, C. et al., "WWOX Gene Expression Abolishes Ovarian Cancer Tumorigenicity in Vivo and Decreases Attachment to Fibronectin via Integrin α3," Cancer Research, Jun. 2009, pp. 4835-4842, vol. 69, No. 11.
Griffiths-Jones, S. et al., "miRBase: MicroRNA Sequences, Targets and Gene Nomenclature," Nucleic Acids Research, 2006, pp. D140-D144, vol. 34.
Guimaraes-Sternberg, C. et al., "MicroRNA Modulation of Megakaryoblast Fate Involves Cholinergic Signaling," Leukemia Research, 2006, pp. 583-595, vol. 30.
Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.
Havelange, V. et al., "MicroRNAs: New Players in Acute Myeloid Leukemia," British Journal of Cancer, 2009, pp. 743-748, vol. 101.
Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.
Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.
Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.
Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.
Iliopoulos, D. et al., "Fragile Genes as Biomarkers: Epigenetic Control of WwWOX and FHIT in Lung, Breast and Bladder Cancer," Oncogene, 2005, pp. 1625-1633, vol. 24.
Iliopoulos, D. et al., "Inhibition of Breast Cancer Growth InVitro and in Vivo: Effect of Restoration of WWOX Expression," Clin. Cancer Research, Jan. 2007, pp. 268-274, vol. 13, No. 1.
Iorio, M. V. et al., "MicroRNA Gene Expression Deregulation in Human Breast Cancer," Cancer Research, Aug. 2005, pp. 7065-7070, vol. 65, No. 16.
Iorio, M. V. et al., "MicroRNA Signatures in Human Ovarian Cancer," Cancer Research, Sep. 2007, pp. 8699-8707, vol. 67, No. 18.
Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.
Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.
Ji, J. et al., "MicroRNA Expression, Survival, and Response to Interferon in Liver Cancer," The New England Journal of Medicine, Oct. 2009, pp. 1437-1447, vol. 361, No. 15.
Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.
Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.
Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.
Jiang, J. et al., "Real-Time Expression Profiling of MicroRNA Precursors in Human Cancer Cell Lines," Nucleic Acids Research, 2005, pp. 5394-5403, vol. 33, No. 17.
John, B. et al., "Human MicroRNA Targets," PLOS Biology, Nov. 2004, pp. 1862-1879, vol. 2, Issue 11.
Johnson, S. M. et al., "RAS is Regulated by the let-7 MicroRNA Family," Cell, Mar. 2005, pp. 635-647, vol. 120.
Johnson, S. M. et al., "RAS is Regulated by the let-7 MicroRNA Family," Supplemental Data, Cell, Mar. 2005, pp. 635-647, vol. 120.
Kawasaki, H. et al., "MicroRNA-196 Inhibits HOXB8 Expression in Myeloid Differentiation of HL60 Cells," Nucleic Acids Symposium Series, 2004, pp. 211-212, No. 48.
Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.
Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007, Los Angeles, CA: AACR, 2007, 2 pages, Abstract No. 1780.
Koturbash, I. et al., "Role of Epigenetic Effectors in Maintenance of the Long-Term Persistent Bystander Effect in Spleen in Vivo," Carcinogenesis, 2007, pp. 1831-1838, vol. 28, No. 8.
Krek, A. et al., "Combinatorial MicroRNA Target Predictions," Nature Genetics, May 2005, pp. 495-500, vol. 37, No. 5.
Kulshreshtha, R. et al., "A MicroRNA Signature of Hypoxia," Molecular and Cellular Biology, Mar. 2007, pp. 1859-1867, vol. 27, No. 5.
Kuroki, et al., "Genetic Alterations of the Tumor Suppressor Gene WWOX in Esophageal Squamous Cell Carcinoma," Cancer Research, Apr. 2002, pp. 2258-2260, vol. 62.
Kutay, H. et al., "Downregulation of miR-122 in the Rodent and Human Hepatocellular Carcinomas," Journal of Cellular Biochemistry, 2006, pp. 671-678, vol. 99.
Lagos-Quintana, M. et al., "New MicroRNAs From Mouse to Human," RNA, 2003, pp. 175-179, vol. 9, No. 2.
Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.
Lee, E. J. et al., "Expression Profiling Identifies MicroRNA Signature in Pancreatic Cancer," Int. J. Cancer, 2006, pp. 1046-1054, vol. 120.
Lewis, B. P. et al., "Prediction of Mammalian MicroRNA Targets," Cell, Dec. 2003, pp. 787-798, vol. 115.
Lin, R.-K. et al., "Alteration of DNA Methyltransferases Contributes to 5'CpG Methylation and Poor Prognosis in Lung Cancer," Lung Cancer, 2007, pp. 205-213, vol. 55.
Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.

Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.
Lu, J. et al., "MicroRNA Expression Profiles Classify Human Cancers," Nature, Jun. 2005, pp. 834-838, vol. 435, Supplementary Information.
Lu, J. et al., "MicroRNA Expression Profiles Classify Human Cancers," Nature, Jun. 2005, pp. 834-838, vol. 435.
Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.
Mack, G. S., "MicroRNA Gets Down to Business," Nature Biotechnology, Jun. 2007, pp. 631-638, vol. 25, No. 6.
Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.
Marcucci, et al., "MicroRNA Expression in Cytogenetically Normal Acute Myeloid Leukemia," NEJM, May 2008, pp. 1919-1928, vol. 358, No. 18.
Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.
McManus, M. T., "MicroRNAs and Cancer," Seminars in Cancer Biology, 2003, pp. 253-258, vol. 13.
Megraw, M. et al., "miRGen: A Database for the Study of Animal MicroRNA Genomic Organization and Function," Nucleic Acids Research, 2007, pp. D149-D155, vol. 35.
Meng, F. et al., "Involvement of Human MicroRNA in Growth and Response to Chemotherapy in Human Cholangiocarcinoma Cell Lines," Gastroenterology, 2006, pp. 2113-2129, vol. 130.
Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.
Michael, M. Z. et al., "Reduced Accumulation of Specific MicroRNAs in Colorectal Neoplasia," Molecular Cancer Research, Oct. 2003, pp. 882-891, vol. 1.
Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.
Mitchell, P. S. et al., "Circulating MicroRNAs as Stable Blood-Based Markers for Cancer Detection," PNAS, Jul. 2008, pp. 10513-10518, vol. 105, No. 30.
Mitrovic, T. et al., "Cancer Gene Therapy," Arch. Oncology, 2005, pp. 23-26, vol. 13, No. 1.
Mountzios, G. et al., "Mechanisms of Disease: Signal Transduction in Lung Carcinogenesis-A Comparison of Smokers and Never-Smokers," Nature Clinical Practice Oncology, Oct. 2008, pp. 610-618, vol. 5, No. 10.
Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.
Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.
Negrini, M. et al., "MicroRNAs in Human Cancer: From Research to Therapy," Journal of Cell Science, Apr. 2007, pp. 1833-1840, vol. 120.
Notice of Allowance and Fees Due in U.S. Appl. No. 12/160,064, filed Jul. 3, 2008, mailing date Nov. 20, 2009.
Notice of Allowance and Fees Due in U.S. Appl. No. 12/298,221, filed Nov. 10, 2008, mailing date Nov. 30, 2009.
Office Action issued in U.S. Appl. No. 12/083,067, filed Jun. 20, 2008, mailing date Jul. 8, 2010.
Office Action issued in U.S Appl. No. 12/160,034 filed Jul. 3, 2008, mailing date Jun. 7, 2010.
Office Action issued in U.S. Appl. No. 12/160,061, filed Jul. 3, 2008, mailing date Mar. 12, 2010.
Office Action issued in U.S. Appl. No. 12/160,061, filed Jul. 3, 2008, mailing date Apr. 24, 2009.
Office Action issued in U.S. Appl. No. 12/160,061, filed Jul. 3, 2008, mailing date Oct. 30, 2009.
Office Action issued in U.S. Appl. No. 12/160,064, filed Jul. 3, 2008, mailing date Aug. 10, 2009.
Office Action issued in U.S. Appl. No. 12/293,471, filed Oct. 9, 2008, mailing date Jun. 8, 2010.
Office Action issued in U.S. Appl. No. 12/373,358, filed Feb. 11, 2009, mailing date Aug. 20, 2010.
Office Action issued in U.S. Appl. No. 12/442,018, filed Mar. 27, 2009, mailing date Apr. 15, 2010.
Palamarchuk, A. et al., "Akt Phosphorylates Tcl1 Oncoprotein and Inhibits Its Repressor Activity," Cancer Research, Jun. 2005, pp. 4515-4519, vol. 65, No. 11.
Pawelczyk, T. et al., "Expression in *Escherichia coli* and Simple Purification of Human Fhit Protein," Protein Expr. Purlf., Apr. 2000, pp. 320-326, vol. 18, No. 3.
PCT International Preliminary Report on Patentability, PCT/US/2007/023660 filed Nov. 1, 2007, dated May 5, 2009.
PCT International Preliminary Report on Patentability, PCT/US/2008/072081 filed Aug. 4, 2008, dated Feb. 9, 2010.
PCT International Preliminary Report on Patentability, PCT/US2006/029889 filed Jul. 31, 2006, dated Feb. 5, 2008.
PCT International Preliminary Report on Patentability, PCT/US2006/035100 filed Sep. 11, 2006, dated Mar. 18, 2008.
PCT International Preliminary Report on Patentability, PCT/US2006/038824 filed Oct. 4, 2006, dated Apr. 9, 2008.
PCT International Preliminary Report on Patentability, PCT/US2007/000024 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2007/006824 filed Mar. 19, 2007, dated Sep. 23, 2008.
PCT International Preliminary Report on Patentability, PCT/US2007/009910 filed Apr. 24, 2007, dated Oct. 28, 2008.
PCT International Preliminary Report on Patentability, PCT/US2007/015892 filed Jul. 12, 2007, dated Jan. 13, 2009.
PCT International Preliminary Report on Patentability, PCT/US2007/020215 filed Sep. 17, 2007, dated Mar. 24, 2009.
PCT International Preliminary Report on Patentability, PCT/US2008/001157 filed Jan. 29, 2008, dated Aug. 4, 2009.
PCT International Preliminary Report on Patentability, PCT/US2008/005503 filed Apr. 29, 2008, dated Nov. 3, 2009.
PCT International Preliminary Report on Patentability, PCT/US2008/007196 filed Jun. 9, 2008, dated Dec. 11, 2009.
PCT International Preliminary Report on Patentability, PCT/US2008/066870 filed Jun. 13, 2008, dated Dec. 17, 2009.
PCT International Preliminary Report on Patentability, PCT/US2008/071532 filed Jul. 30, 2008, dated Feb. 2, 2010.
PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Preliminary Report on Patentability, PCT/US2009/035458 filed Feb. 27, 2009, dated Aug. 31, 2010.
PCT International Preliminary Report on Patentability, PCT/US2009/035463 filed Feb. 27, 2009, dated Aug. 31, 2010.
PCT International Preliminary Report on Patentability, PCT/US2009/035470 filed Feb. 27, 2009, dated Aug. 31, 2010.
PCT International Preliminary Report on Patentability, PCT/US2009/035482 filed Feb. 27, 2009, dated Aug. 31, 2010.
PCT International Search Report and the Written Opinion, PCT/US2007/006824 filed Mar. 19, 2007, dated Mar. 3, 2008.
PCT International Search Report and the Written Opinion, PCT/US2006/29889 filed Jul. 31, 2006, dated Jul. 10, 2007.

PCT International Search Report and the Written Opinion, PCT/US2006/35100 filed Sep. 11, 2006, dated Sep. 5, 2007.
PCT International Search Report and the Written Opinion, PCT/US2006/38824 filed Oct. 4, 2006, dated Aug. 9, 2007.
PCT International Search Report and the Written Opinion, PCT/US2007/00024 filed Jan. 3, 2007, dated Nov. 5, 2007.
PCT International Search Report and the Written Opinion, PCT/US2007/00103 filed Jan. 3, 2007, dated Dec. 3, 2007.
PCT International Search Report and the Written Opinion, PCT/US2007/00159 filed Jan. 3, 2007, dated Apr. 11, 2008.
PCT International Search Report and the Written Opinion, PCT/US2007/006824 filed Mar. 19, 2007, dated May 14, 2008.
PCT International Search Report and the Written Opinion, PCT/US2007/09910 filed Apr. 24, 2007, dated Feb. 13, 2008.
PCT International Search Report and the Written Opinion, PCT/US2007/15892 filed Jul. 12, 2007, dated Sep. 30, 2008.
PCT International Search Report and the Written Opinion, PCT/US2007/20215 filed Sep. 17, 2007, dated Jul. 25, 2008.
PCT International Search Report and the Written Opinion, PCT/US2007/23660 filed Nov. 1, 2007, dated Sep. 16, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.
PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2008/72081 filed Aug. 4, 2008, dated Jan. 14, 2009.
PCT International Search Report and the Written Opinion, PCT/US2008/73964 filed Aug. 22, 2008, dated Dec. 24, 2008.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/81294 filed Oct. 27, 2008, dated Mar. 26, 2009.
PCT International Search Report and the Written Opinion, PCT/US2008/84821 filed Nov. 26, 2008, dated Feb. 17, 2009.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2009/38214 filed Mar. 25, 2009, dated Aug. 14, 2009.
PCT International Search Report and the Written Opinion, PCT/US2009/46999 filed Jun. 11, 2009, dated Nov. 23, 2009.
PCT International Search Report and the Written Opinion, PCT/US2009/53586 filed Aug. 12, 2009, dated Oct. 28, 2009.
PCT International Search Report and the Written Opinion, PCT/US2009/65072 filed Nov. 19, 2009, dated Mar. 3, 2010.
PCT International Search Report and the Written Opinion, PCT/US2010/025173 filed Feb. 24, 2010, dated Jul. 6, 2010.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Animal Models for Chronic Lymphocytic Leumekia," Journal of Cellular Biochemistry, 2007, pp. 1109-1118, vol. 100.
Pekarsky, Y. et al., "Tcl1 Enhances Akt Kinase Activity and Mediates Its Nuclear Translocation," PNAS, Mar. 2000, pp. 3028-3033, vol. 97, No. 7.
Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.
Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.
Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.
Prueitt, R. L. et al., "Expression of MicroRNAs and Protein-Coding Genes Associated with Perineural Invasion in Prostate Cancer," The Prostate, 2008, pp. 1152-1164, vol. 68.
Qin, H. R. et al., "A Role for the WWOX Gene in Prostate Cancer," Cancer Research, Jul. 2006, pp. 6477-6481, vol. 66, No. 13.
Ramkissoon, S. H, et al., "Hematopoietic-Specific MicroRNA Expression in Human Cells," Leukemia Research, 2006, pp. 643-647, vol. 30.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.
Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.
Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.
Schmittgen, T. D. et al., "A High-Throughput Method to Monitor the Expression of MicroRNA Precursors," Nucleic Acids Research, Feb. 2004, vol. 32, No. 4.
Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.
Seike, M. et al., "MiR-21 is an EGFR-Regulated Anti-Apoptotic Factor in Lung Cancer in Never-Smokers," Supporting Information, PNAS, Jul. 2009, pp. 12085-12090. vol. 106, No. 29.
Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.
Seth, P., "Vector-Mediated Cancer Gene Therapy," Cancer Biology & Therapy, May 2005, pp. 512-517, vol. 4, Issue 5.
Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.
Sharma, S. et al., "Development of Inhalational Agents for Oncologic Use," Journal of Clinical Oncology, Mar. 2001, Abstract, vol. 19, Issue 6.
Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.
Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.
Tang, X. et al., "A Simple Array Platform for MicroRNA Analysis and Its Application in Mouse Tissues," RNA, Aug. 2007, pp. 1-20, vol. 13.
Thomson, J. M. et al., "A Custom Microarray Platform for Analysis of MicroRNA Gene Expression," Nature Methods, Oct. 2004, pp. 1-7, vol. 1, No. 1.
Thorgeirsson, S. S. et al., "Functional Genomics of Hepatocellular Carcinoma," Hepatology, Feb. 2006, pp. S145-S150, vol. 43, No. 2, Suppl. 1.
Tockman, M. S. et al., "Considerations in Bringing a Cancer Biomarker to Clinical Application," Cancer Research, May 1992, pp. 2711s-2718s, vol. 52.
Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.
Tricoli, J. V. et al., "MicroRNA: Potential for Cancer Detection, Diagnosis, and Prognosis," Cancer Research, May 2007, pp. 4553-4555, vol. 67, No. 10.
Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.
Valeri, N. et al., "Epigenetics, miRNAs, and Human Cancer: A New Chapter in Human Gene Regulation," Mamm Genome, Aug. 2009, pp. 573-580, vol. 20.
Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.
Virgilio, L. et al., "Identification of the TCL1 Gene Involved in T-Call Malignancies," Proc. Natl. Acad. Sci., Dec. 1994, pp. 12530-12534, vol. 91.
Visone, R. et al., "MiRNAs and Cancer," The American Journal of Pathology, Apr. 2009, pp. 1131-1138, vol. 174, No. 4.
Volinia, et al., "Reprogramming of MirRNA Networks in Cancer and Leukemia," Genome Research, 2010, pp. 589-599, vol. 20.
Volinia, S. et al., "A MicroRNA Expression Signature of Human Solid Tumors Defines Cancer Gene Targets," PNAS, Feb. 2006, pp. 2257-2261, vol. 103, No. 7.
Wang, E. et al., "Ontogeny and Oncogenesis Balance the Transcriptional Profile of Renal Cell Cancer," Cancer Research, Oct. 2004, pp. 7279-7287, vol. 64.
Wang, X. et al., "Association Between CpG Island Methylation of the WWOX Gene and Its Expression in Breast Cancers," Tumor Biology, Feb. 2009, pp. 8-14, vol. 30.
Weidhaas, J., "Using MicroRNAs to Understand Cancer Biology," Published Online Dec. 21, 2009, DOI: 10.1016/S1470-2045(09)70386-9.
Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.
Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.
Yanaihara, N. et al., "Unique MicroRNA Molecular Profiles in Lung Cancer Diagnosis and Prognosis," Cancer Cell, Mar. 2006, pp. 189-198, vol. 9.
Yang, J. et al., "Analysis of Sequence Variations in 59 MicroRNAs in Hepatocellular Carcinomas," Mutation Research, Aug. 2008, pp. 205-209, vol. 638.
Yendamuri, S. et al., "WW Domain Containing Oxidoreductase Gene Expression is Altered in Non-Small Cell Lung Cancer," Cancer Research, Feb. 2003, pp. 878-881, vol. 63.
Yoon, S. et al., "Prediction of Regulatory Modules Comprising MicroRNAs and Target Genes," Bioinformatics Genes and Genomes, 2005. pp. ii93-ii100, vol. 21, Suppl. 2.
Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.
Zeng, Y. et al., "Recognition and Cleavage of Primary MicroRNA Precursors by the Nuclear Processing Enzyme Drosha," The EMBO Journal, 2005, pp. 138-148, vol. 24.
Zhang, L. et al., "Genomic and Epigenetic Alterations Deregulate MicroRNA Expression in Human Epithelial Ovarian Cancer," PNAS, May 2008, pp. 7004-7009, vol. 105, No. 19.
Zhang, L. et al., "MicroRNAs Exhibit High Frequency Genomic Alterations in Human Cancer," PNAS, Jun. 2006, pp. 9136-9141, vol. 103, No. 24.
Zhang, L. et al., Supporting Information, PNAS 2008, pp. 1-11.
Zhang, Z. et al., "Three Biomarkers Identified from Serum Proteomic Analysis for the Detection of Early Stage Ovarian Cancer," Cancer Research, Aug. 2004, pp. 5882-5890, vol. 64.
Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
European Search Report, Application No. 08713330.2, dated Jul. 22, 2011.

* cited by examiner

1E

1F

| Characteristic | 122 AML patients Value | Validation set (36) patients Value |
|---|---|---|
| **Age** | | |
| Median | 60.3 | 55.17 |
| Range | (18-86) | (20-78) |
| **Sex - no. (%)** | | |
| Female | 47(38) | 19(53) |
| Male | 75(62) | 17(47) |
| **White cell count x$10^9$ /L** | | |
| Median | 46.83 | 68.1 |
| Range | (0.7-278) | (1.2-147) |
| **Bone marrow blasts count %** | | |
| Median | 62 | 69 |
| Range | 20-99 | (20-98) |
| **FAB** | | |
| M0 | 7 (5) | 2 (5.5) |
| M1 | 12 (10) | 5 (14) |
| M2 | 22 (18) | 11(30.5) |
| M3 | 4 (3) | 0 |
| M4 | 38 (31) | 7(19) |
| M5 | 15 (12) | 3 (8.4) |
| M6 | 11 (9) | 1(2.8) |

Figure 4 - Table 1

| | | |
|---|---|---|
| M7 | 5 (4) | 1(2.8) |
| Not determined* | 8 (6) | 6 (17) |
| **Cytogenetics †** | | |
| t(15;17) (q22;q21) | 4 (3.4) | 0 |
| inv(16)/ t(16;16) | 4 (34) | 0 |
| Normal Karyotype | 45 (39) | 12 (33.7) |
| 11q23 rearrangements | 9 (7.8) | 3 (8.4) |
| -7 | 4 (3.4) | 0 |
| -5 | 1 (0.8) | 0 |
| del 5(q) | 3 (2.6) | 1(2.8) |
| del 9(q) | 2 (1.7) | 1(2.8) |
| del 13 (q12;q22) | 2 (1.7) | 0 |
| +8 | 5 (4.4) | 1 (2.8) |
| +4 | 2 (1.7) | 0 |
| Complex karyotype‡ | 25 (21.5) | 11 (30.5) |
| Other abnormal karyotypes | 10 (8.6) | 7 (19) |
| **Vital status –no/ (%)** | | |
| **Dead** | 81 (66) | 28 (77) |
| **Alive** | 41 (33) | 8 (23) |

Figure 4 continued - Table 1

| MicroRNA | Group Signature | Location | Putative targets |
|---|---|---|---|
| *miR-181a,b* | Up in AML M0-M1 | 9q33 | *RUNX1,KIT* |
| *miR-146* | Up in AML M0-M1 | 5q33 | *KIT, SDFR1* |
| *miR-145* | Up in AML M6-M7, Down in M4-M5 | 5q32 | *FLI1, CBFB* |
| *miR-126* | Up in AML M6-M7 and complex karyotype | 9q34 | *Crk, HOXA9* |
| | Down in normal karyotype and M4-M5 | | |
| *miR-135b* | Down in t(15;17) | 1q32 | *LTZS1,AKT3* |
| *miR-10a* | Up in normal karyotype | 17q21 | *HOXA1, VEGFR* |
| *miR-10b* | Up in normal karyotype | 2q31 | *HOXA1, VEGFR* |
| *miR-326* | Up in 11q23 rearrangements. | 11q13 | *CEBPA, RAP1B* |
| *miR-194* | Up in 11q23 rearrangements | 11q13 | *MEIS1, EIF2C1* |
| *miR-29b* | Down in 11q23 rearrangements | 7q32 | *MCL1, DNMT3B* |
| *miR-34b* | Down in 11q23 , Up in normal karyotype | 11q23 | *NOTCH1, MYB* |
| *MiR-124a* | Up in +8 | 8p23 | *SP3, MITF* |
| *MiR-30d* | Up in +8 | 8q24 | *RARB,JUNB* |

Figure 5 - Table 2

| *MicroRNA* | Expression in patients with short survival | Genomic Location | *Putative targets* |
|---|---|---|---|
| *miR-25* | High | 7q22 | *JUN,GATA2* |
| *miR-20* | High | 13q31 | *E2F3, RUNX1* |
| *miR-17-5p* | High | 13q31 | *E2F3, RUNX1* |
| *miR-182* | High | 7q32 | *MITF, CEBPA* |
| *miR-199a* | High | 19q13 | *RUNX1, PAX3* |
| *miR-199b* | High | 9q34 | *RUNX1, PAX3* |
| *miR-191* | High | 3p21 | *CEBPB,MECP* |

Figure 6 - Table 3

| ID | Name |
|---|---|
| *HSHELA01* | Human HeLa cell Jo-1 tRNA-His (GUG) |
| *HSTRNL* | Human transfer RNA-Leu (MAA) |
| *HSU2SNRNA3P* | H.sapiens U2 snRNA |
| *HSU2SNRNA5P* | H.sapiens U2 snRNA |
| *HSU4SNRNA3P* | H.sapiens U4 snRNA |
| *HSU4SNRNA5P* | H.sapiens U4 snRNA |
| *HSU6SNRNA3P* | H.sapiens U6 snRNA |
| *HSU6SNRNA5P* | H.sapiens U6 snRNA |
| *Human GAPDH* | H.sapiens GAPDH |
| *HUMTRAB* | Human Ala-tRNA |
| *HUMTRF* | Human Phe-tRNA |
| *HUMTRMI No1* | Human initiator Met-tRNA-i |
| *HUMTRMI No2* | Human initiator Met-tRNA-i |
| *HUMTRMI3P* | Human initiator Met-tRNA-i |
| *HUMTRMI5P* | Human initiator Met-tRNA-i |
| *HUMTRN* | Human Asn-tRNA |
| *HUMTRS* | Human transfer RNA-Ser |
| *HUMTRV1A* | Human Val-tRNA-1a |

Figure 7 - Table 4

| Down-regulated in AML | SAM Score* | Fold Change | FDR (%)† |
|---|---|---|---|
| *hsa-mir-126* | -3.28 | 0.21 | 0 |
| *hsa-mir-130a* | -2.90 | 0.29 | 0 |
| *hsa-mir-130b prec* | -2.56 | 0.37 | 0 |
| *hsa-mir-135* | -2.55 | 0.38 | 0 |
| *hsa-mir-93* | -2.52 | 0.08 | 0 |
| *hsa-mir-146* | -2.47 | 0.41 | 0 |
| *hsa-mir-106b* | -2.43 | 0.36 | 0 |
| *hsa-mir-224* | -2.39 | 0.32 | 0 |
| *hsa-mir-125a* | -2.18 | 0.50 | 0 |
| *hsa-mir-92* | -2.13 | 0.46 | 0 |
| *hsa-mir-106a* | -2.12 | 0.46 | 0 |
| *hsa-mir-95* | -2.07 | 0.04 | 0 |
| *hsa-mir-155* | -2.03 | 0.49 | 0 |
| *hsa-mir-25* | -2.01 | 0.50 | 0 |
| *hsa-mir-96* | -1.94 | 0.25 | 0 |
| *hsa-mir-124a* | -1.92 | 0.37 | 0 |
| *hsa-mir-18* | -1.89 | 0.38 | 0 |
| *hsa-mir-20* | -1.87 | 0.50 | 0 |
| *hsa-let-7d* | -1.80 | 0.48 | 0 |
| *hsa-mir-26a* | -1.76 | 0.48 | 0 |
| *hsa-mir-128b-prec* | -1.72 | 0.32 | 0 |
| *hsa-mir-222* | -1.71 | 0.50 | 0 |
| *hsa-mir-101* | -1.67 | 0.50 | 0 |
| *hsa-mir-338* | -1.54 | 0.31 | 0 |
| *hsa-mir-184-prec* | -1.52 | 0.48 | 0 |
| *hsa-mir-371* | -1.51 | 0.38 | 0 |
| *hsa-mir-199b* | -1.44 | 0.03 | 0 |
| *hsa-mir-29b* | -1.40 | 0.12 | 0 |
| *hsa-mir-301* | -1.37 | 0.47 | 0 |

* SAM identifies genes with statistically significant changes in expression by assimilating a set of gene-specific scores (i.e. paired *t* tests). Each gene is assigned a score on the basis of its change in gene expression relative to the standard deviation of repeated measurements for that gene. Genes with scores greater than a threshold are deemed potentially significant.

† The percentage of such genes identified by chance is the q-value o False Discovery Rate.

Figure 8 - Table 5

| | MicroRNA | Sam Score | Fold Change | FDR (%) |
|---|---|---|---|---|
| * | *hsa-mir-181c* | 2.58 | 2.78 | 0 |
| * | *hsa-mir-181a* | 2.49 | 2.71 | 0 |
| | *hsa-mir-30b* | 2.48 | 2.66 | 0 |
| * | *hsa-mir-192* | 2.46 | 4.89 | 0 |
| | *hsa-mir-130a* | 2.45 | 2.53 | 0 |
| | *hsa-mir-30c* | 2.44 | 2.71 | 0 |
| * | *hsa-mir-146* | 2.40 | 2.11 | 0 |
| | *hsa-mir-30c-prec* | 2.31 | 2.67 | 0 |
| * | *hsa-mir-26a- prec* | 2.26 | 2.15 | 0 |
| * | *hsa-mir-181b* | 1.99 | 2.67 | 0 |
| * | *hsa-mir-124a* | 1.99 | 2.16 | 0 |
| * | *hsa-mir-128b* | 1.95 | 2.83 | 0 |

All miRNAs are up-regulated.
* MiRNAs found also up-regulated in treated AML patients with FAB M0-M1 vs. other FAB subtypes.

Figure 9 - Table 6

| MicroRNA | SAM Score | Fold Change | FDR (%) |
|---|---|---|---|
| *hsa-mir-135b* | -3.51 | 0.36 | 0 |
| *hsa-mir-99b-prec* | -2.25 | 0.35 | 0 |
| *hsa-mir-132-prec* | -2.19 | 0.28 | 0 |
| *hsa-mir-95* | -1.93 | 0.07 | 0 |
| *hsa-let-7d* | -1.75 | 0.3 | 0 |

All miRNAs are down-regulated.

Figure 10 - Table 7

| miRNA | SAM Score | Fold Change | FDR (%) |
|---|---|---|---|
| *hsa-mir-21* | 2.53 | 2.52 | 0 |
| *hsa-miR-126* | -2.85 | 0.49 | 0 |
| *hsa-mir-331-prec* | -2.55 | 0.45 | 0 |
| *hsa-mir-145* | -2.37 | 0.38 | 0 |
| *hsa-mir-143* | -2.35 | 0.44 | 0 |
| *hsa-mir-193* | -2.33 | 0.37 | 0 |
| *hsa-mir-340* | -2.04 | 0.44 | 0 |
| *hsa-mir-204* | -1.90 | 0.43 | 0 |
| *hsa-mir-206* | -1.90 | 0.47 | 0 |
| *hsa-mir-29c* | -1.86 | 0.48 | 0 |
| *hsa-mir-188* | -1.81 | 0.50 | 0 |
| *hsa-mir-204-prec* | -1.76 | 0.37 | 0 |
| *hsa-mir-128a* | -1.75 | 0.48 | 2.5 |
| *hsa-mir-202* | -1.74 | 0.48 | 2.5 |
| *hsa-mir-194* | -1.72 | 0.45 | 2.5 |
| *hsa-mir-299* | -1.72 | 0.48 | 2.5 |
| *hsa-mir-126-prec* | -1.71 | 0.36 | 2.5 |
| *hsa-mir-190* | -1.71 | 0.45 | 2.5 |
| *hsa-mir-183-prec* | -1.54 | 0.45 | 2.5 |

MiRNAs in red are up-regulated, in green down-regulated.
All miRNAs except *miR-21* and *mR-331* were also found differentially expressed in treated AML patients with FAB M4-M5 compared with other FAB subtypes.

Figure 11 - Table 8

| | miRNA | SAM Score | Fold Change | FDR (%) |
|---|---|---|---|---|
| * | *hsa-mir-126* | 4.61 | 4.42 | 0 |
| | *hsa-mir-204* | 4.58 | 3.51 | 0 |
| | *hsa-mir-190* | 4.27 | 3.51 | 0 |
| * | *hsa-mir-145* | 4.22 | 5.22 | 0 |
| | *hsa-mir-183-prec* | 4.19 | 2.72 | 0 |
| | *hsa-mir-205* | 4.18 | 2.66 | 0 |
| | *hsa-mir-196b* | 4.11 | 3.32 | 0 |
| | *hsa-mir-203-prec* | 4.09 | 2.44 | 0 |
| | *hsa-mir-200c* | 3.94 | 2.29 | 0 |
| | *hsa-mir-206* | 3.92 | 3.07 | 0 |
| | *hsa-mir-203* | 3.92 | 2.53 | 0 |
| * | *hsa-mir-125a-prec* | 3.89 | 2.79 | 0 |
| | *hsa-mir-204-prec* | 3.87 | 2.92 | 0 |
| | *hsa-mir-197* | 3.85 | 3.09 | 0 |
| | *hsa-mir-188* | 3.85 | 2.62 | 0 |
| * | *hsa-mir-143* | 3.75 | 3.16 | 0 |
| | *hsa-let-7a-2-prec* | -3.95 | 0.12 | 0 |
| * | *hsa-mir-181b* | -3.82 | 0.30 | 0 |
| * | *hsa-mir-26a* | -3.77 | 0.02 | 0 |
| | *hsa-mir-30b* | -3.54 | 0.32 | 0 |
| | *hsa-mir-181c* | -3.37 | 0.27 | 0 |
| | *hsa-mir-181b* | -3.01 | 0.28 | 0 |
| | *hsa-mir-30c-prec* | -3.01 | 0.20 | 0 |
| | *hsa-mir-30c* | -2.85 | 0.35 | 0 |
| * | *hsa-mir-34bNo2* | -2.83 | 0.03 | 0 |
| | *hsa-mir-23a* | -2.79 | 0.50 | 0 |
| | *hsa-mir-324* | -2.60 | 0.27 | 0 |
| | *hsa-mir-21* | -2.60 | 0.22 | 0 |
| | *hsa-mir-181b-prec* | -2.57 | 0.45 | 0 |
| | *hsa-mir-16-2* | -2.55 | 0.41 | 0 |

MiRNAs in red are up-regulated, in green down-regulated.
* These miRNAs were found also differentially expressed in treated AML patients (4) with FAB M6-M7 subtype compared with all the other FAB subtypes (48).

Figure 12 - Table 9

| miRNA correlated with high WBC | SAM Score | FDR (%) |
|---|---|---|
| *hsa-mir-155* | 2.96 | 0 |
| *hsa-mir-30e* | 2.79 | 0 |
| *hsa-mir-23b* | 2.73 | 0 |
| *hsa-mir-181b* | 2.59 | 0 |
| *hsa-mir-213* | 2.59 | 0 |
| *hsa-mir-221* | 2.58 | 0 |
| *hsa-mir-29b* | 2.58 | 0 |
| *hsa-mir-95* | 2.56 | 0 |
| *hsa-mir-128b* | 2.54 | 0 |
| *hsa-mir-27a* | 2.52 | 0 |
| *hsa-mir-181c* | 2.52 | 0 |
| *hsa-mir-92* | 2.45 | 0 |
| *hsa-mir-181a* | 2.44 | 0 |
| *hsa-mir-23a* | 2.43 | 0 |
| *hsa-mir-214* | 2.42 | 0 |
| *hsa-mir-30b* | 2.39 | 0 |
| *hsa-mir-30c* | 2.36 | 0 |
| *hsa-mir-26b* | 2.35 | 0 |
| *hsa-mir-21* | 2.33 | 0 |
| *hsa-mir-222* | 2.32 | 0 |
| **miRNAs correlated with high BM blasts %** | | |
| *hsa-mir-30b* | 4.54 | 0 |
| *hsa-mir-30c* | 4.31 | 0 |
| *hsa-mir-192* | 3.95 | 0 |
| *hsa-mir-181a* | 3.90 | 0 |
| *hsa-mir-155* | 3.82 | 0 |
| *hsa-let-7a-2* | 3.73 | 0 |
| *hsa-mir-181b* | 3.69 | 0 |
| *hsa-mir-181b-prec* | 3.65 | 0 |
| *hsa-mir-34b* | 3.65 | 0 |
| *hsa-mir-181c* | 3.64 | 0 |
| *hsa-mir-219* | 3.55 | 0 |
| *hsa-mir-214* | 3.51 | 0 |
| *hsa-mir-213* | 3.49 | 0 |
| *hsa-mir-301No2* | 3.38 | 0 |
| *hsa-mir-26a* | 3.37 | 0 |
| **miRNAs correlated with high peripheral blasts %** | | |
| *hsa-mir-133b* | 2.97 | 0 |
| *hsa-mir-213* | 2.91 | 0 |
| *hsa-mir-214* | 2.75 | 0 |
| *hsa-mir-25* | 2.71 | 0 |
| *hsa-mir-181a* | 2.63 | 0 |
| *hsa-mir-181b* | 2.54 | 0 |

Figure 13 - Table 10

| | | |
|---|---|---|
| *hsa-mir-220* | 2.42 | 0 |
| *hsa-mir-92* | 2.39 | 0 |
| *hsa-mir-184* | 2.28 | 0 |
| *hsa-mir-92* | 2.26 | 0 |
| *hsa-mir-124a* | 2.22 | 0 |
| *hsa-mir-129-prec* | 2.22 | 0 |
| *hsa-mir-100* | 2.20 | 0 |
| *hsa-mir-181b* | 2.12 | 0 |
| *hsa-mir-135* | 2.01 | 0 |
| *hsa-mir-155* | 2.00 | 0 |
| *hsa-mir-222* | 1.93 | 0 |
| *hsa-mir-181c* | 1.85 | 0 |

All miRNAs are up-regulated (red) and have a positive correlation with WBC count, PB and BM blast percentage. These results were obtained by using quantitative SAM analysis. MiRNAs highlighted in yellow are shared in at least two signatures.

Figure 13 continued - Table 10

| MicroRNA | SAM Score | Fold Change | FDR (%) |
|---|---|---|---|
| *hsa-mir-34b* | 4.27 | 3.03 | 0 |
| *hsa-mir-10a* | 3.64 | 4.07 | 0 |
| *hsa-mir-10b* | 3.48 | 3.13 | 0 |
| *hsa-mir-26a* | 3.42 | 2.72 | 0 |
| *hsa-mir-30c* | 3.41 | 2.26 | 0 |
| *hsa-let-7a-2* | 3.24 | 2.25 | 0 |
| *hsa-mir-16-2* | 2.92 | 2.02 | 0 |
| *hsa-mir-21* | 2.84 | 2.58 | 0 |
| *hsa-mir-181b* | 2.54 | 2.21 | 0 |
| *hsa-mir-368* | 2.02 | 2.68 | 0 |
| *hsa-mir-192* | 1.97 | 2.75 | 0 |
| *hsa-mir-126* | -3.85 | 0.31 | 0 |
| *hsa-mir-203* | -3.21 | 0.41 | 0 |
| *hsa-mir-200c* | -3.10 | 0.45 | 0 |
| *hsa-mir-200c-prec* | -3.03 | 0.39 | 0 |
| *hsa-mir-203-prec* | -3.00 | 0.43 | 0 |
| *hsa-mir-182* | -3.00 | 0.38 | 0 |
| *hsa-mir-198-prec* | -2.98 | 0.36 | 0 |
| *hsa-mir-204* | -2.98 | 0.41 | 0 |
| *hsa-mir-205-prec* | -2.97 | 0.5 | 0 |
| *hsa-mir-183-prec* | -2.96 | 0.42 | 0 |
| *hsa-mir-196b* | -2.94 | 0.42 | 0 |
| *hsa-mir-193* | -2.80 | 0.42 | 0 |
| *hsa-mir-182-prec* | -2.78 | 0.38 | 0 |
| *hsa-mir-191* | -2.76 | 0.43 | 0 |
| *hsa-mir-199a* | -2.70 | 0.42 | 0 |
| *hsa-mir-194* | -2.61 | 0.36 | 0 |
| *hsa-mir-204-prec* | -2.60 | 0.24 | 0 |
| *hsa-mir-183* | -2.56 | 0.28 | 0 |
| *hsa-mir-299* | -2.55 | 0.43 | 0 |
| *hsa-mir-193-prec* | -2.43 | 0.45 | 0 |
| *hsa-mir-30b-prec* | -2.28 | 0.55 | 0 |

All miRNAs, except *miR-368* and *miR-192* were found also differentially expressed in treated AML patients with normal karyotype (10) compared with treated AML patients with abnormal karyotype (38).

MiRNAs in red are up-regulated, in green down-regulated.

Figure 14 - Table 11

| MicroRNA | SAM Score | Fold Change | FDR (%) |
|---|---|---|---|
| *hsa-mir-326* | 3.74 | 5.49 | 0 |
| *hsa-mir-219* | 2.42 | 2.60 | 6.2 |
| *hsa-mir-194* | 2.24 | 2.73 | 6.2 |
| *hsa-mir-301* | 2.19 | 2.65 | 6.2 |
| *hsa-miR-324* | 2.05 | 2.33 | 6.9 |
| *hsa-mir-339* | 2.04 | 2.51 | 6.9 |
| *hsa-mir-99b* | 1.86 | 2.03 | 7.3 |
| *hsa-mir-328* | 1.80 | 2.31 | 7.6 |
| *hsa-mir-34b* | -5.46 | 0.12 | 0 |
| *hsa-mir-15a* | -4.13 | 0.11 | 0 |
| *hsa-mir-29a* | -4.00 | 0.10 | 0 |
| *hsa-mir-29c* | -3.98 | 0.02 | 0 |
| *hsa-mir-372* | -3.68 | 0.15 | 0 |
| *hsa-mir-30a* | -3.62 | 0.18 | 0 |
| *hsa-mir-29b* | -3.60 | 0.02 | 0 |
| *hsa-mir-30e* | -3.58 | 0.13 | 0 |
| *hsa-mir-196a* | -3.57 | 0.39 | 0 |
| *hsa-let-7f* | -3.52 | 0.20 | 0 |
| *hsa-mir-102* | -3.40 | 0.01 | 0 |
| *hsa-mir-331* | -3.36 | 0.10 | 0 |
| *hsa-mir-299* | -3.04 | 0.01 | 0 |
| *hsa-mir-29a-prec* | -3.00 | 0.16 | 0 |
| *hsa-mir-193* | -2.86 | 0.04 | 0 |

MiRNAs in red are up-regulated, in green down-regulated.
The same signature was observed in an independent set of treated patients *with 11q23* (4) vs. other cytogenetic abnormalities (44), except *miR-372, miR-196a and miR-193*.

Figure 15 - Table 12

| | miRNA | SAM Score(d) | Fold Change | FDR (%) |
|---|---|---|---|---|
| * | *hsa-mir-126* | 3.03 | 2.71 | 0 |
| * | *hsa-mir-193* | 3.00 | 2.19 | 0 |
| * | *hsa-mir-204* | 2.96 | 2.39 | 0 |
| * | *hsa-mir-9-3* | 2.51 | 2.08 | 0 |
| | *hsa-mir-145* | 2.45 | 2.20 | 0 |
| * | *hsa-mir-128a-prec* | 2.11 | 2.13 | 0 |
| | *hsa-mir-30c* | -2.90 | 0.30 | 0 |
| * | *hsa-mir-301* | -2.83 | 0.32 | 0 |
| | *hsa-mir-30b* | -2.62 | 0.35 | 0 |
| | *hsa-mir-30c-prec* | -2.57 | 0.33 | 0 |
| | *hsa-mir-23a-prec* | -2.50 | 0.46 | 0 |
| * | *hsa-mir-26a* | -2.36 | 0.49 | 0 |
| | *hsa-mir-10a* | -2.26 | 0.17 | 0 |
| * | *hsa-mir-26a-prec* | -2.18 | 0.47 | 0 |
| | *hsa-mir-16-2* | -2.06 | 0.46 | 0 |
| | *hsa-mir-222-prec* | -1.94 | 0.49 | 0 |
| | *hsa-mir-16-1* | -1.93 | 0.45 | 0 |
| | *hsa-mir-10b-prec* | -1.87 | 0.28 | 0 |
| | *hsa-mir-30e* | -1.84 | 0.48 | 0 |
| | *hsa-mir-21* | -1.77 | 0.49 | 0 |
| | *hsa-mir-155* | -1.62 | 0.49 | 0 |
| | *hsa-mir-181c* | -1.61 | 0.46 | 0 |
| | *hsa-mir-10a-prec* | -1.24 | 0.49 | 2.3 |
| | *hsa-mir-192* | -1.20 | 0.44 | 2.3 |

MiRNAs in red are up-regulated, in green down-regulated.
* These miRNAs were also found differentially expressed in treated patients with complex karyotype (14) vs. non complex, including normal karyotype (34).

Figure 16 - Table 13

| miRNA | SAM Score | Fold Change | FDR (%) |
|---|---|---|---|
| *hsa-mir-204* | 2.27 | 2.15 | 0 |
| *hsa-mir-126* | 2.26 | 4.03 | 0 |
| *hsa-mir-205* | 2.19 | 2.05 | 0 |
| *hsa-mir-190* | 2.14 | 2.46 | 0 |
| *hsa-let-7d* | 2.12 | 2.62 | 0 |
| *hsa-mir-196a* | 1.95 | 2.42 | 0 |
| *hsa-mir-197* | 1.95 | 2.00 | 0 |
| *hsa-mir-188* | 1.89 | 2.13 | 0 |
| *hsa-mir-204-prec* | 1.87 | 2.89 | 0 |
| *hsa-mir-125a-prec* | 1.86 | 2.38 | 0 |
| *hsa-mir-18* | 1.64 | 6.05 | 2.53 |
| *hsa-mir-186* | 1.55 | 2.74 | 4.21 |
| *hsa-mir-196a prec* | 1.54 | 2.05 | 4.21 |
| *hsa-mir-9* | 1.49 | 2.02 | 4.21 |

All miRNAs are up-regulated.

Figure 17 - Table 14

| miRNA | SAM Score | Fold Change | FDR (%) |
|---|---|---|---|
| *hsa-mir-337* | 3.49 | 29.94 | 0 |
| *hsa-mir-192-prec* | 3.41 | 13.49 | 0 |
| *hsa-mir-337-prec* | 3.25 | 14.05 | 0 |
| *hsa-mir-184* | 3.21 | 25.49 | 0 |
| *hsa-mir-302b* | 3.06 | 4.93 | 0 |
| *hsa-mir-206-prec* | 2.95 | 13.16 | 0 |
| *hsa-mir-105* | 2.94 | 11.05 | 0 |
| *hsa-let-7d* | 2.87 | 8.85 | 0 |
| *hsa-mir-153* | 2.86 | 14.2 | 0 |
| *hsa-mir-124a* | 2.78 | 10.67 | 0 |
| *hsa-mir-215* | 2.69 | 13.19 | 0 |
| *hsa-mir-1* | 2.68 | 199.7 | 0 |
| *hsa-mir-194* | 2.62 | 18.13 | 0 |
| *hsa-mir-199b-prec* | 2.61 | 9.87 | 0 |
| *hsa-mir-29c* | 2.59 | 8.19 | 0 |

Figure 18 - Table 15

| | | | |
|---|---|---|---|
| *hsa-mir-208* | 2.56 | 11.65 | 0 |
| *hsa-mir-199a* | 2.54 | 14.01 | 0 |
| *hsa-mir-24-1* | 2.49 | 5.21 | 0 |
| *hsa-miR-302c* | 2.47 | 6.37 | 0 |
| *hsa-mir-338-prec* | 2.42 | 5.67 | 0 |
| *hsa-mir-367* | 2.41 | 9.11 | 0 |
| *hsa-mir-200a* | 2.41 | 4.19 | 0 |
| *hsa-mir-183* | 2.38 | 33.93 | 0 |
| *hsa-mir-199b* | 2.38 | 7.23 | 0 |
| *hsa-mir-372-prec* | 2.35 | 6.11 | 0 |
| *hsa-mir-143* | 2.35 | 5.56 | 0 |
| *hsa-mir-96* | 2.31 | 11.59 | 0 |
| *hsa-mir-204-prec* | 2.26 | 6.16 | 0 |
| *hsa-mir-29b* | 2.26 | 6.91 | 0 |
| *hsa-mir-202* | 2.25 | 5.64 | 0 |
| *hsa-mir-340* | 2.23 | 4.75 | 0 |
| *hsa-mir-102* | 2.17 | 8.11 | 0 |
| *hsa-mir-191* | 2.13 | 9.48 | 0 |
| *hsa-let-7i* | 2.11 | 6.78 | 0 |
| *hsa-mir-184-prec* | 2.11 | 5.69 | 0 |
| *hsa-miR-302b-prec* | 2.11 | 4.76 | 0 |
| *hsa-mir-30a* | 2.09 | 2.84 | 0 |
| *hsa-mir-9-3* | 2.08 | 4.11 | 0 |
| *hsa-mir-26a-prec* | 2.07 | 3.72 | 0 |
| *hsa-mir-124a-3* | 2.07 | 7.55 | 0 |
| *hsa-mir-203* | 2.03 | 6.99 | 0 |
| *hsa-mir-302a* | 2.02 | 11.36 | 0 |
| *hsa-mir-199a* | 2.01 | 8.93 | 0 |
| *hsa-mir-206* | 1.99 | 4.55 | 0 |
| *hsa-mir-197* | 1.98 | 5.25 | 0 |
| *hsa-mir-198* | 1.97 | 12.42 | 0 |
| *hsa-mir-372* | 1.95 | 4.99 | 0.68 |
| *hsa-mir-182* | 1.95 | 9.29 | 0.68 |
| *hsa-mir-129-prec* | 1.95 | 8.72 | 0.68 |
| *hsa-mir-193* | 1.92 | 8.72 | 0.68 |
| *hsa-mir-325* | 1.92 | 2.82 | 0.68 |
| *hsa-mir-183-prec* | 1.92 | 7.61 | 0.68 |
| *hsa-mir-196b-prec* | 1.92 | 4.89 | 0.68 |
| *hsa-mir-182-prec* | 1.92 | 8.62 | 0.68 |
| *hsa-mir-192* | 1.89 | 8.6 | 0.68 |
| *hsa-mir-367-prec* | 1.87 | 2.82 | 0.68 |

Figure 18 continued - Table 15

| | | | |
|---|---|---|---|
| *hsa-mir-299-prec* | 1.87 | 6.83 | 0.68 |
| *hsa-mir-200c-prec* | 1.85 | 6.65 | 0.68 |
| *hsa-mir-204* | 1.84 | 5.11 | 0.68 |
| *hsa-mir-299* | 1.84 | 3.37 | 0.68 |
| *hsa-mir-29a* | 1.83 | 2.29 | 1 |
| *hsa-mir-203-prec* | 1.77 | 6.73 | 1 |
| *hsa-mir-331-prec* | 1.76 | 3.81 | 1 |
| *hsa-mir-95* | 1.75 | 3.52 | 1 |
| *hsa-mir-30d-prec* | 1.73 | 2.04 | 1 |
| *hsa-mir-200c* | 1.72 | 5.72 | 1 |
| *hsa-mir-205* | 1.71 | 5.41 | 1 |
| *hsa-mir-196a-prec* | 1.67 | 3.76 | 1 |
| *hsa-mir-17-prec* | 1.66 | 1.97 | 1 |
| *hsa-mir-103* | 1.65 | 2.56 | 1 |
| *hsa-mir-193-prec* | 1.63 | 4.16 | 1 |
| *hsa-mir-93* | 1.61 | 2.66 | 1 |
| *hsa-mir-373-prec* | 1.57 | 2.92 | 1 |
| *hsa-mir-190* | 1.54 | 5.38 | 1 |
| *hsa-miR-373* | 1.53 | 3.24 | 1 |
| *hsa-mir-196b-prec* | 1.53 | 3.66 | 1 |
| *hsa-mir-154* | 1.48 | 4.06 | 1.88 |
| *hsa-mir-19b-1* | 1.47 | 2.48 | 1.88 |
| *hsa-mir-196-1* | 1.46 | 2.88 | 1.88 |
| *hsa-let-7i* | 1.46 | 1.67 | 1.88 |
| *hsa-mir-324* | 1.42 | 2.84 | 1.88 |
| *hsa-mir-371-prec* | 1.34 | 2.95 | 2.75 |

* These miRNAs are located at Chromosome 8.
For this analysis we included only samples with isolated trisomy 8. These samples were compared with other AML samples with known cytogenetics, excluding those samples with trisomy 8 as a secondary cytogenetics abnormality.
All miRNAs are up-regulated.

Figure 18 continued - Table 15

| Characteristic | | Value |
|---|---|---|
| **AGE** | | 52 |
| | | (18-83) |
| **Sex** | female | 25(46) |
| | Male | 29(54) |
| **White count x $10^9$ / L** | | |
| | median | 50.3 |
| | range | (2.4-335) |
| **Bone marrow blasts %** | | 64.2 |
| | | (20-99) |
| **FAB no. (%)** | | |
| | M0 | 1(1.8) |
| | M1 | 10(18) |
| | M2 | 15(28) |
| | M4 | 8(15) |
| | M5 | 2(3.7) |
| | M6 | 3(5.5) |
| | M7 | 2(3.7) |
| | Unknown | 13(24) |
| **Cytogenetics** | | |
| | normal karyotype | 10(18) |
| | -7 | 1(1.8) |
| | 11q23 rearrangements | 4(7) |
| | t (6;9)(p23;q34) | 2(3.7) |
| | +8 | 5(9) |
| | complex karyotype | 15(27) |
| | Other | 10(20) |
| | Not done | 7(13) |
| **Patient Status** | | |
| | Primary refractory | 20(37) |
| | Relapsed | 34(63) |

Figure 19 - Table 16

Figure 20:
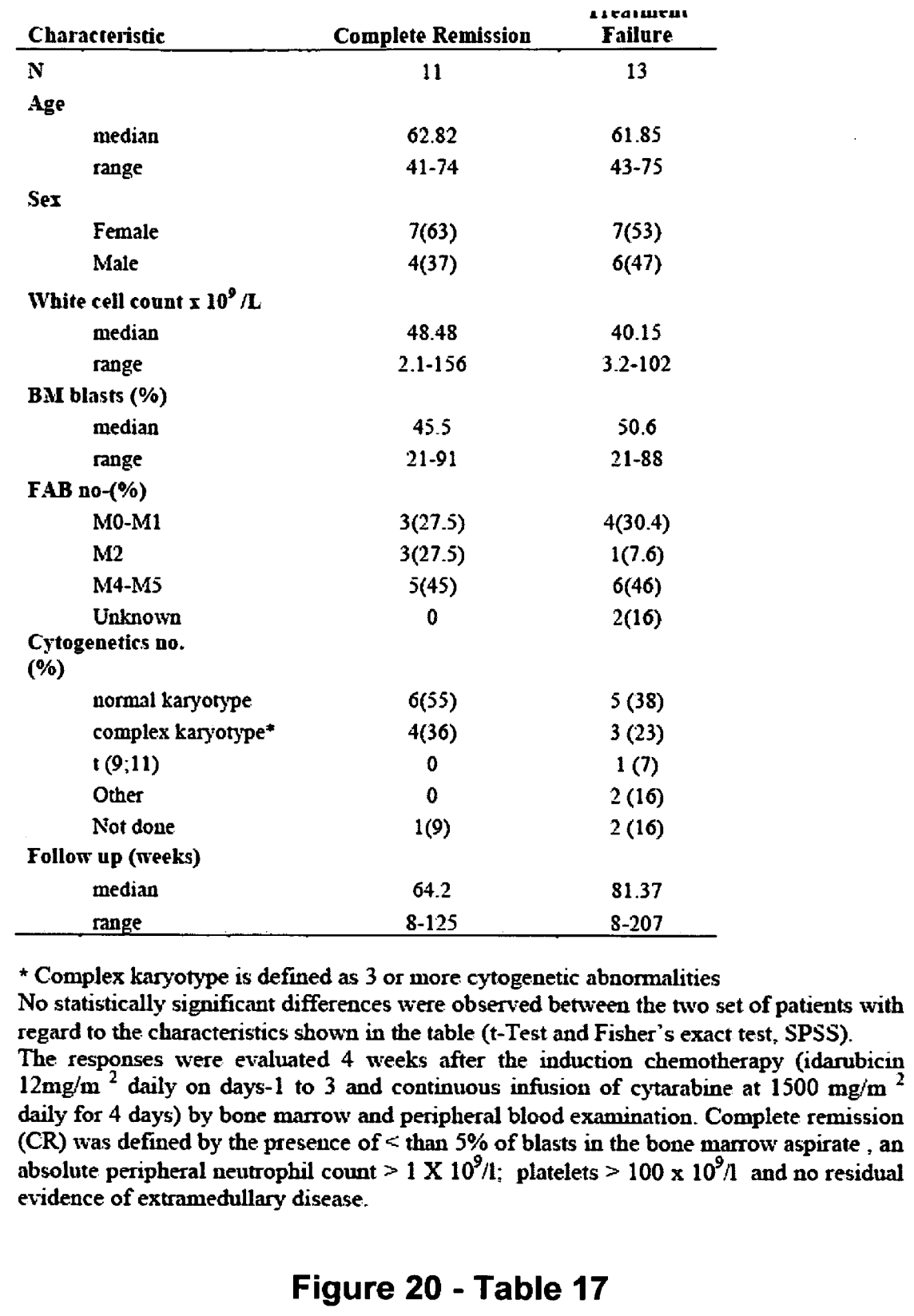

| Characteristic | Complete Remission | Treatment Failure |
|---|---|---|
| N | 11 | 13 |
| **Age** | | |
| median | 62.82 | 61.85 |
| range | 41-74 | 43-75 |
| **Sex** | | |
| Female | 7(63) | 7(53) |
| Male | 4(37) | 6(47) |
| **White cell count x $10^9$ /L** | | |
| median | 48.48 | 40.15 |
| range | 2.1-156 | 3.2-102 |
| **BM blasts (%)** | | |
| median | 45.5 | 50.6 |
| range | 21-91 | 21-88 |
| **FAB no-(%)** | | |
| M0-M1 | 3(27.5) | 4(30.4) |
| M2 | 3(27.5) | 1(7.6) |
| M4-M5 | 5(45) | 6(46) |
| Unknown | 0 | 2(16) |
| **Cytogenetics no. (%)** | | |
| normal karyotype | 6(55) | 5 (38) |
| complex karyotype* | 4(36) | 3 (23) |
| t (9;11) | 0 | 1 (7) |
| Other | 0 | 2 (16) |
| Not done | 1(9) | 2 (16) |
| **Follow up (weeks)** | | |
| median | 64.2 | 81.37 |
| range | 8-125 | 8-207 |

* Complex karyotype is defined as 3 or more cytogenetic abnormalities

No statistically significant differences were observed between the two set of patients with regard to the characteristics shown in the table (t-Test and Fisher's exact test, SPSS).

The responses were evaluated 4 weeks after the induction chemotherapy (idarubicin 12mg/m $^2$ daily on days-1 to 3 and continuous infusion of cytarabine at 1500 mg/m $^2$ daily for 4 days) by bone marrow and peripheral blood examination. Complete remission (CR) was defined by the presence of < than 5% of blasts in the bone marrow aspirate , an absolute peripheral neutrophil count > 1 X $10^9$/l; platelets > 100 x $10^9$/l and no residual evidence of extramedullary disease.

Figure 20 - Table 17

| MicroRNA | SAM Score | Fold Change | FDR (%) |
|---|---|---|---|
| *hsa-mir-183* | -3.04 | 5.50 | 0 |
| *hsa-mir-208-prec* | -2.99 | 3.20 | 0 |
| *hsa-mir-184* | -2.96 | 5.60 | 0 |
| *hsa-mir-29b* | -2.92 | 3.10 | 0 |
| *hsa-mir-194* | -2.89 | 4.30 | 0 |
| *hsa-mir-183-prec* | -2.73 | 3.20 | 0 |
| *hsa-mir-205* | -2.71 | 3.10 | 0 |
| *hsa-mir-337* | -2.66 | 4.30 | 0 |
| *hsa-mir-199a* | -2.65 | 3.50 | 0 |
| *hsa-mir-199a-prec* | -2.64 | 3.10 | 0 |
| *hsa-mir-193* | -2.61 | 3.10 | 0 |
| *hsa-mir-204* | -2.59 | 4.50 | 0 |
| *hsa-mir-203* | -2.58 | 3.10 | 0 |
| *hsa-mir-182* | -2.57 | 3.10 | 0 |
| *hsa-mir-299-prec* | -2.57 | 3.10 | 0 |
| *hsa-mir-198* | -2.57 | 2.70 | 0 |
| *hsa-mir-337-prec* | -2.55 | 3.50 | 0 |
| *hsa-mir-203-prec* | -2.55 | 2.70 | 0 |
| *hsa-mir-204-prec* | -2.55 | 2.90 | 0 |
| *hsa-mir-200c* | -2.55 | 2.90 | 0 |
| *hsa-mir-200cprec* | -2.54 | 2.60 | 0 |
| *hsa-mir-192* | -2.46 | 2.70 | 0 |
| *hsa-mir-199b* | -2.45 | 2.60 | 0 |
| *hsa-mir-182-prec* | -2.45 | 2.50 | 0 |
| *hsa-mir-29c* | -2.38 | 2.60 | 0 |

All miRNAs are down-regulated in patients who did not achieve complete remission after induction with Idarubicin and cytarabine.

Figure 21 - Table 18

MICRORNA-BASED METHODS AND COMPOSITIONS FOR THE DIAGNOSIS, PROGNOSIS AND TREATMENT OF ACUTE MYELOID LEUKEMIA (AML)

BACKGROUND OF THE INVENTION

Acute myeloid leukemia (AML) is a heterogeneous disorder that includes many entities with diverse genetic abnormalities and clinical features[1]. The pathogenesis is known for relatively few types of leukemia[2]. Patients with intermediate and poor risk cytogenetics represent the majority of AML; chemotherapy based regimens fail to cure most of these patients and stem cell transplantation is frequently the treatment choice[3-4]. Since allogeneic stem cell transplantation is not an option for many patients with high risk leukemia, there is a critical need to improve our understanding of the biology of these leukemias and to develop improved therapies.

Systematic high-throughput analysis of mRNA expression levels in AML has described new molecular subgroups of AML; some of these have been suggested to predict outcome[5-6]. Despite this progress, focusing on known genes will likely not suffice to uncover the molecular puzzle of AML. The integration of a whole genome approach including non-coding RNAs may lead to an improved understanding of AML biology.

MicroRNAs (miRNAs) are non-coding RNAs of 19-25 nucleotides in length that regulate gene expression by inducing translational inhibition or cleavage of their target mRNA through base pairing to partially or fully complementary sites[7]. The miRNAs are involved in critical biological processes, including development, cell differentiation, apoptosis and proliferation[8]. Recently, miRNA expression has been linked to hematopoiesis and cancer[9-11]. Calin et al. have shown deletions and down-regulation of miR-15a and miR-16-1 in chronic lymphocytic leukemia[12]. Several groups have reported changes in miRNA expression in large cell lymphoma[13] and pediatric Burkitt lymphoma[14]. More recently, it has been shown that over-expression of miR-155 in B cells of transgenic mice results in polyclonal B cell proliferation and B cell neoplasia[15]. These observations indicate that miRNAs are involved in the initiation and progression of human cancer.

As disclosed herein, miRNA microarrays are used to profile a large set of AML patients with predominately intermediate and poor prognosis to investigate the association of miRNA profiles with cytogenetic groups and clinical features.

Identification of microRNAs that are differentially-expressed in acute myeloid leukemia cancer cells would aid in diagnosing, prognosticating and treating leukemia. Furthermore, the identification of putative targets of these miRNAs would help to unravel their pathogenic role. In one broad aspect, there is provided herein provides novel methods and compositions for the diagnosis, prognosis and treatment of acute myeloid leukemia.

SUMMARY OF THE INVENTION

The present invention is based, in part, on the identification of an acute myeloid leukemia cancer-specific signature of miRNAs that are differentially-expressed in breast cancer cells, relative to normal control cells.

Accordingly, the invention encompasses methods of diagnosing whether a subject has, or is at risk for developing, acute myeloid leukemia (AML), comprising measuring the level of at least one miR gene product in a test sample from said subject, wherein an alteration in the level of the miR gene product in the test sample, relative to the level of a corresponding miR gene product in a control sample, is indicative of the subject either having, or being at risk for developing, AML.

In certain embodiments, at least one miR gene product is miR-29 or miR-181. In certain embodiments, the at least one miR gene product is miR-29b and/or miR-181b.

The level of the at least one miR gene product can be measured using a variety of techniques that are well known to those of skill in the art. In one embodiment, the level of the at least one miR gene product is measured using Northern blot analysis. In another embodiment, the level of the at least one miR gene product in the test sample is less than the level of the corresponding miR gene product in the control sample. Also, in another embodiment, the level of the at least one miR gene product in the test sample can be greater than the level of the corresponding miR gene product in the control sample.

The invention also provides methods of diagnosing a AML associated with one or more prognostic markers in a subject, comprising measuring the level of at least one miR gene product in a AML sample from said subject, wherein an alteration in the level of the at least one miR gene product in the test sample, relative to the level of a corresponding miR gene product in a control sample, is indicative of the subject having a AML associated with the one or more prognostic markers. In one embodiment, the level of the at least one miR gene product is measured by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal of at least one miRNA is indicative of the subject either having, or being at risk for developing, AML.

The invention also encompasses methods of treating CLL in a subject, wherein the signal of at least one miRNA, relative to the signal generated from the control sample, is de-regulated (e.g., down-regulated, up-regulated).

In certain embodiments, a microarray comprises miRNA-specific probe oligonucleotides for one or more miRNAs selected from the group consisting of miR-29 or miR-181 and combinations thereof.

The invention also encompasses methods of diagnosing whether a subject has, or is at risk for developing, a AML associated with one or more adverse prognostic markers in a subject, by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for said test sample; and, comparing the test sample hybridization profile to a hybridization profile generated from a control sample. An alteration in the signal is indicative of the subject either having, or being at risk for developing, the cancer.

The invention also encompasses methods of treating AML in a subject who has AML in which at least one miR gene product is down-regulated or up-regulated in the cancer cells of the subject relative to control cells. When the at least one miR gene product is down-regulated in the cancer cells, the method comprises administering to the subject an effective amount of at least one isolated miR gene product, such that proliferation of cancer cells in the subject is inhibited. When the at least one miR gene product is up-regulated in the cancer cells, the method comprises administering to the subject an effective amount of at least one compound for inhibiting expression of the at least one miR gene product, such that proliferation of cancer cells in the subject is inhibited. In certain embodiments, the at least one isolated miR gene product is selected miR-29, miR-181 and combinations thereof.

In related embodiments, the invention provides methods of treating AML in a subject, comprising: determining the amount of at least one miR gene product in AML cells, relative to control cells; and altering the amount of miR gene product expressed in the AML cells by: administering to the subject an effective amount of at least one isolated miR gene product, if the amount of the miR gene product expressed in the cancer cells is less than the amount of the miR gene product expressed in control cells; or administering to the subject an effective amount of at least one compound for inhibiting expression of the at least one miR gene product, if the amount of the miR gene product expressed in the cancer cells is greater than the amount of the miR gene product expressed in control cells, such that proliferation of cancer cells in the subject is inhibited. In certain embodiments, at least one isolated miR gene product is selected from the group consisting of miR-29, miR-181, and combinations thereof.

The invention further provides pharmaceutical compositions for treating AML, comprising at least one isolated miR gene product and a pharmaceutically-acceptable carrier. In a particular embodiment, the pharmaceutical compositions the at least one isolated miR gene product corresponds to a miR gene product that is down-regulated in AML cells relative to suitable control cells. In particular embodiments, the pharmaceutical composition is selected from the group consisting of miR-29, miR-181 and combinations thereof. In another particular embodiment, the pharmaceutical composition comprises at least one miR expression inhibitor compound and a pharmaceutically-acceptable carrier. Also, in a particular embodiment, the pharmaceutical composition comprises at least one miR expression inhibitor compound is specific for a miR gene product that is up-regulated in AML cells relative to suitable control cells.

In other embodiments, the present invention provides methods of identifying an anti-AML agent, comprising providing a test agent to a cell and measuring the level of at least one miR gene product associated with decreased expression levels in AML cells, wherein an increase in the level of the miR gene product in the cell, relative to a suitable control cell, is indicative of the test agent being an anti-AML agent. In certain embodiments, the miR gene product is selected from the group consisting of at least one miR gene product is selected from the group consisting of the miRNAs as shown in any one of FIGS. 5-6, 8-18 and 21 (Tables 1-2, 5-15 and 18). In a particular embodiment, least one miR gene product is selected from the group consisting of miR-20, miR-25, miR-191, miR-199a, and miR-199b and combinations thereof.

The present invention also provides methods of identifying an anti-AML agent, comprising providing a test agent to a cell and measuring the level of at least one miR gene product associated with increased expression levels in AML cells, wherein an decrease in the level of the miR gene product in the cell, relative to a suitable control cell, is indicative of the test agent being an anti-AML agent. In a particular embodiment, the miR gene product is selected from the group consisting of miR-29, miR-181 and combinations thereof.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

FIG. 1A. MicroRNA (miRNA) expression of 6 AML samples with respect to CD34+ progenitors. Results are presented as fold change of the miRNA expression in AML samples with respect to CD34+ expression values, after normalization (Ct) with let-7i and $2^{\Delta Ct}$ conversion[18] (thin bars represent standard deviations).

FIG. 1B. Validation of the microarrays data using qRT-PCR. Scatter plot showing the negative correlation between the miRNA micro array s expression values (2 log) and the normalized qRT-PCR OCt values (log scale) for each sample (Pearson correlation coefficient R=0.88 p<0.001). The solid pink line represents the predicted Y. The lower the qRT-PCR (Ct values), the higher the expression level of the miRNA. For example, the points at the bottom right have low ΔCt values (high expression) and correspond with high micro array (chip) values.

FIG. 1C. MiRNA expression in mature and hematopoietic committed precursors with respect to CD34+ stem cells. The results are presented as fold change in the average miRNA expression of the different mature and committed precursors with respect to that of CD34+ cells after normalization with 18S and $2^{\Delta Ct}$ conversion.

FIG. 1D. Average qRT-PCR expression of miR-181b in AML samples grouped according the FAB classification; the numbers of patient samples in each category are as follows; M0-M1 (6), M2 (8) and M 6M7 (5).

FIG. 1E. Average miR-10 qRT-PCR expression in AML patients with normal karyotype (10) vs. other abnormal karyotype (26).

FIG. 1F. Average expression of miR-126 in patients with complex karyotype (6) and in patients with other cytogenetic abnormalities (22) by qRT-PCR. The miRNA expression between the different groups was compared by using t-Test (SPSS).

FIG. 4. Table 1. Clinical and cytogenetics characterizations of 158 newly diagnosed patients with AML.

FIG. 5. Table 2. MicroRNAs associated with FAB classification and cytogenetics.

FIG. 6. Table 3. MicroRNAs associated with overall survival in 122 patients with AML.

FIG. 7. Table 4. Housekeeping gene probes used in the normalization of microarray data.

FIG. 8. Table 5. MiRNAs differentially expressed between CD 34+ cells and the 122 patients with AML.

FIG. 9 (Table 6). MiRNAs differentially expressed in AML FAB M0-M1 compared with others AML FAB subtypes.

FIG. 10. Table 7. MiRNAs differentially expressed in AML FAB M3 [t (15; 17)].

FIG. 11. Table 8. MiRNAs differentially expressed in A ML FAB M4 and M5 compared with other AML.

FIG. 12. Table 9. MiRNAs differentially expressed in AML FAB M6 and M7 compared with other AML.

FIG. 13. Table 10. MiRNAs associated with high WBC, and peripheral blood (PB) and bone marrow (BM) blasts.

FIG. 14. Table 11. MiRNAs differentially expressed in normal karyotype AML compared with other AML.

FIG. 15. Table 12. MiRNAs associated with 11q23 rearrangements.

FIG. 16. Table 13. MiRNAs differentially expressed in patients with complex karyotype compared with non-complex or normal karyotype.

FIG. 17. Table 14. MiRNAs associated with chromosome 7.

FIG. 18. Table 15. MiRNAs associated with trisomy 8.

FIG. 19. Table 16. Characteristics of 54 patients with AML at first relapse after initial induction chemotherapy or primary refractory disease.

FIG. 20. Table 17. Clinical characteristics of the 24 patients treated with idarubicin and cytarabine.

FIG. 21. Table 18. MiRNAs associated with response to Idarubicin and cytarabine.

DESCRIPTION OF THE INVENTION

Figure 1A:
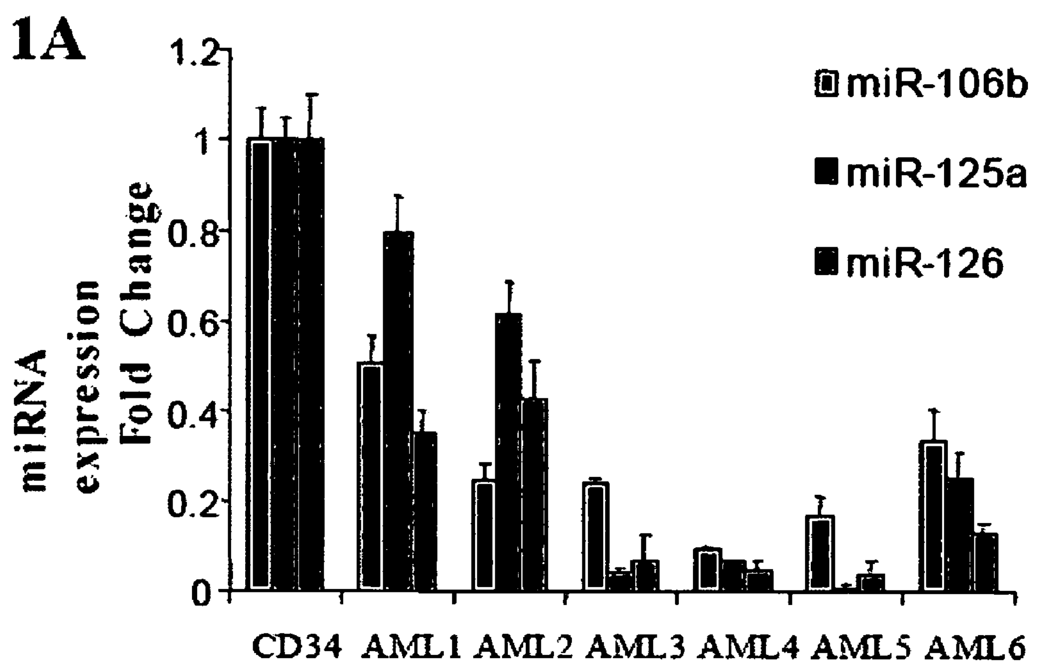
FIGS. 1A-F. Validation of microarray data by quantification of mature miRNAs by qRT-PCR.

The present invention is based, in part, on the identification of particular microRNAs having altered expression in acute myeloid leukemia (AML) cancer cells relative to normal control cells, and on association of these microRNAs with particular diagnostic, prognostic and therapeutic features.

As used herein interchangeably, a "miR gene product," "microRNA," "miR," or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

The present invention encompasses methods of diagnosing whether a subject has, or is at risk for developing, AML, comprising measuring the level of at least one miR gene product in a test sample from the subject and comparing the level of the miR gene product in the test sample to the level of a corresponding miR gene product in a control sample. As used herein, a "subject" can be any mammal that has, or is suspected of having, AML. In a preferred embodiment, the subject is a human who has, or is suspected of having, AML.

The level of at least one miR gene product can be measured in cells of a biological sample obtained from the subject. For example, a tissue sample can be removed from a subject suspected of having AML by conventional biopsy techniques. In another embodiment, a blood sample can be removed from the subject, and white blood cells can be isolated for DNA extraction by standard techniques. The blood or tissue sample is preferably obtained from the subject prior to initiation of radiotherapy, chemotherapy or other therapeutic treatment. A corresponding control tissue or blood sample, or a control reference sample, can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. Alternatively, a reference sample can be obtained and processed separately (e.g., at a different time) from the test sample and the level of a miR gene product produced from a given miR gene in cells from the test sample can be compared to the corresponding miR gene product level from the reference sample.

In one embodiment, the level of the at least one miR gene product in the test sample is greater than the level of the corresponding miR gene product in the control sample (i.e., expression of the miR gene product is "up-regulated"). As used herein, expression of a miR gene product is "up-regulated" when the amount of miR gene product in a cell or tissue sample from a subject is greater than the amount of the same gene product in a control cell or tissue sample. In another embodiment, the level of the at least one miR gene product in the test sample is less than the level of the corresponding miR gene product in the control sample (i.e., expression of the miR gene product is "down-regulated"). As used herein, expression of a miR gene is "down-regulated" when the amount of miR gene product produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

An alteration (i.e., an increase or decrease) in the level of a miR gene product in the sample obtained from the subject, relative to the level of a corresponding miR gene product in a control sample, is indicative of the presence of AML cancer in the subject. In one embodiment, the level of at least one miR gene product in the test sample is greater than the level of the corresponding miR gene product in the control sample. In another embodiment, the level of at least one miR gene product in the test sample is less than the level of the corresponding miR gene product in the control sample.

In a certain embodiment, the at least one miR gene product is selected from the groups as shown in the Tables and Figures herein.

The level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes (e.g., DNA probes, RNA probes) for Northern blot hybridization of a given miR gene product can be produced from the nucleic acid sequences provided in the Tables herein and include, but are not limited to, probes having at least about 70%, 75%, 80%, 85%, 90%, 95%, 98% or 99% complementarity to a miR gene product of interest, as well as probes that have complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^{3}H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^{8}$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in the Tables herein, and include, but are not limited to, probes having at least about 70%, 75%, 80%, 85%, 90%, 95%, 98% or 99% complementarity to a miR gene product of interest, as well as probes that have complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a “housekeeping” gene present in the same sample. A suitable “housekeeping” gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer. Assessing cancer-specific expression levels for hundreds of miR genes or gene products is time consuming and requires a large amount of total RNA (e.g., at least 20 μg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotide) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in AML cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from AML cells, and within AML cells, different prognosis states (for example, good or poor long term survival prospects) may be determined. By comparing expression profiles of AML cells in different states, information regarding which genes are important (including both up- and down-regulation of genes) in each of these states is obtained. The identification of sequences that are differentially expressed in AML cells or normal cells, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient). Similarly, diagnosis may be done or confirmed by comparing patient samples with known expression profiles. Furthermore, these gene expression profiles (or individual genes) allow screening of drug candidates that suppress the AML expression profile or convert a poor prognosis profile to a better prognosis profile.

Accordingly, the invention provides methods of diagnosing whether a subject has, or is at risk for developing, AML, comprising reverse transcribing RNA from a test sample obtained from the subject to provide a set of target oligodeoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample, wherein an alteration in the signal of at least one miRNA is indicative of the subject either having, or being at risk for developing, AML. In one embodiment, the microarray comprises miRNA-specific probe oligonucleotides for a substantial portion of all known human miRNAs.

In a particular embodiment, the microarray comprises miRNA-specific probe oligonucleotides for one or more miRNAs selected from the group consisting of the miRNAs as shown in any one of FIGS. 5-6, 8-18 and 21 (Tables 1-2, 5-15 and 18). In one embodiment, at least one miR gene product is selected from the group consisting of miR-20, miR-25, miR-191, miR-199a, and miR-199b and combinations thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75× TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 μg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer (e.g., AML) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, e.g., noncancerous, control sample. An alteration in the signal is indicative of the presence of, or propensity to develop, cancer in the subject.

Other techniques for measuring miR gene expression are also within the skill in the art, and include various techniques for measuring rates of RNA transcription and degradation.

The invention also provides methods of determining the prognosis of a subject with AML cancer, comprising measuring the level of at least one miR gene product, which is associated with a particular prognosis in AML (e.g., a good or positive prognosis, a poor or adverse prognosis), in a test sample from the subject. According to these methods, an alteration in the level of a miR gene product that is associated with a particular prognosis, in the test sample, as compared to the level of a corresponding miR gene product in a control sample, is indicative of the subject having AML with a particular prognosis. In one embodiment, the miR gene product is associated with an adverse (i.e., poor) prognosis. Examples of an adverse prognosis include, but are not limited to, low survival rate and rapid disease progression.

In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more miR gene products in cells can result in the deregulation of one or more intended targets for these miRs, which can lead to the formation of AML. Therefore, altering the level of the miR gene product (e.g., by decreasing the level of a miR that is up-regulated in AML cancer cells, by increasing the level of a miR that is down-regulated in AML cancer cells) may successfully treat the AML cancer.

Accordingly, the present invention encompasses methods of treating AML in a subject, wherein at least one miR gene product is deregulated (e.g., down-regulated, up-regulated) in the cells (e.g., AML cancer cells) of the subject. In one embodiment, the level of at least one miR gene product in a test sample (e.g., AML cancer sample) is greater than the level of the; corresponding miR gene product in a control sample. In another embodiment, the level of at least one miR gene product in a test sample (e.g., AML cancer sample) is less than the level of the corresponding miR gene product in a control sample. When the at least one isolated miR gene product is down-regulated in the AML cancer cells, the method comprises administering an effective amount of the at least one isolated miR gene product, or an isolated variant or biologically-active fragment thereof, such that proliferation of cancer cells in the subject is inhibited. For example, when a miR gene product is down-regulated in a cancer cell in a subject, administering an effective amount of an isolated miR gene product to the subject can inhibit proliferation of the cancer cell. The isolated miR gene product that is administered to the subject can be identical to an endogenous wild-type miR gene product (e.g., a miR gene product shown in the Tables herein) that is down-regulated in the cancer cell or it can be a variant or biologically-active fragment thereof.

As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with AML (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with AML. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is up-regulated in the cancer cells, the method comprises administering to the subject an effective amount of a compound that inhibits expression of the at least one miR gene product, such that proliferation of AML cancer cells is inhibited. Such compounds are referred to herein as miR gene expression-inhibition compounds. Examples of suitable miR gene expression-inhibition compounds include, but are not limited to, those described herein (e.g., double-stranded RNA, antisense nucleic acids and enzymatic RNA molecules). In a particular embodiment, a miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

In a certain embodiment, the isolated miR gene product that is deregulated in AML cancer is selected from the group consisting of the miRNAs as shown in any one of FIGS. 5-6, 8-18 and 21 (Tables 1-2, 5-15 and 18).

In a particular embodiment, the at least one miR gene product is selected from the group consisting of miR-20, miR-25, miR-191, miR-199a, and miR-199b and combinations thereof.

The terms "treat", "treating" and "treatment", as used herein, refer to ameliorating symptoms associated with a disease or condition, for example, AML cancer, including preventing or delaying the onset of the disease symptoms, and/or lessening the severity or frequency of symptoms of the disease or condition. The terms "subject" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from AML cancer. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product that is administered to a subject can range from about 5-3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in a substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating AML cancer in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol,* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therap.* 2:301-310; Eglitis (1988), *Biotechniques* 6:608-614; Miller (1990), *Hum. Gene Therap.* 1:5-14; and Anderson (1998), *Nature* 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.*, 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in a cancer cell, using, for example, the techniques for determining miR transcript level discussed herein. Inhibition can occur at the level of gene expression (i.e., by inhibiting transcription of a miR gene encoding the miR gene-product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer (e.g., AML cancer). One skilled in the art can readily determine an effective amount of a miR expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject, as described herein.

Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression (e.g., by inhibiting translation, by inducing cleavage and/or degradation) of the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA that is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acids (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product. Nucleic acid sequences of particular human miR gene products are provided in the Tables herein. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucl. Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cancer cells in a subject who has a cancer (e.g., AML). As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibiting compounds. An inhibition of cancer cell proliferation can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The miR gene products or miR gene expression-inhibiting compounds can be administered to a subject by any means suitable for delivering these compounds to cancer cells of the subject. For example, the miR gene products or miR expression-inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression-inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy)

propyl]-N,N,N-trimethyl-ammonium methyl sulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibiting compound can be administered to the subject either as naked RNA, in combination with a delivery reagent, or as a nucleic acid (e.g., a recombinant plasmid or viral vector) comprising sequences that express the miR gene product or miR gene expression-inhibiting compound. Suitable delivery reagents include, e.g., the Mirus Transit TKO lipophilic reagent; LIPOFECTIN; lipofectamine; cellfectin; polycations (e.g., polylysine) and liposomes.

Recombinant plasmids and viral vectors comprising sequences that express the miR gene products or miR gene expression-inhibiting compounds, and techniques for delivering such plasmids and vectors to cancer cells, are discussed herein and/or are well known in the art.

In a particular embodiment, liposomes are used to deliver a miR gene product or miR gene expression-inhibiting compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) or derivatives thereof, e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors (e.g., AML cancers), will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating AML cancer. In one embodiment, the pharmaceutical composition comprises at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in AML cancer cells relative to suitable control cells.

In other embodiments, the pharmaceutical compositions of the invention comprise at least one miR expression-inhibition compound. In a particular embodiment, the at least one miR gene expression-inhibition compound is specific for a miR gene whose expression is greater in AML cancer cells than control cells.

Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example, as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising a sequence encoding the miR gene product or miR gene expression-inhibition compound) (e.g., 0.1 to 90% by weight), or a physiologically-acceptable salt thereof, mixed with a pharmaceutically-acceptable carrier. In certain embodiments, the pharmaceutical composition of the invention additionally comprises one or more anti-cancer agents (e.g., chemotherapeutic agents). The pharmaceutical formulations of the invention can also comprise at least one miR gene product or miR gene expression-inhibition compound (or at least one nucleic acid comprising a sequence encoding the miR gene product or miR gene expression-inhibition compound), which are encapsulated by liposomes and a pharmaceutically-acceptable carrier. In one embodiment, the pharmaceutical composition comprises a miR gene or gene product that is not miR-15, miR-16, miR-143 and/or miR-145.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising a sequence encoding the miR gene product or miR gene expression-inhibition compound) that is resistant to degradation by nucleases. One skilled in the art can readily synthesize nucleic acids that are nuclease resistant, for example by incorporating one or more ribonucleotides that is modified at the 2'-position into the miR gene product. Suitable 2'-modified ribonucleotides include those modified at the 2'-position with fluoro, amino, alkyl, alkoxy and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising a sequence encoding the miR gene product or miR gene expression-inhibition compound) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising a sequence encoding the miR gene product or miR gene expression-inhibition compound) and at least one chemotherapeutic agent. Chemotherapeutic agents that are suitable for the methods of the invention include, but are not limited to, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel and FOLFOX4.

The invention also encompasses methods of identifying an anti-AML cancer agent, comprising providing a test agent to a cell and measuring the level of at least one miR gene product in the cell. In one embodiment, the method comprises providing a test agent to a cell and measuring the level of at least one miR gene product associated with decreased expression levels in AML cancer cells. An increase in the level of the miR gene product in the cell, relative to a suitable control (e.g., the level of the miR gene product in a control cell), is indicative of the test agent being an anti-AML cancer agent.

In a particular embodiment, the at least one miR gene product associated with decreased expression levels in AML cancer cells is selected from the group consisting of the miRNAs as shown in any one of FIGS. 5-6, 8-18 and 21 (Tables 1-2, 5-15 and 18) and a combination thereof.

In other embodiments the method comprises providing a test agent to a cell and measuring the level of at least one miR gene product associated with increased expression levels in AML cancer cells. A decrease in the level of the miR gene product in the cell, relative to a suitable control (e.g., the level of the miR gene product in a control cell), is indicative of the test agent being an anti-AML cancer agent.

In a particular embodiment, at least one miR gene product associated with increased expression levels in AML cancer cells is selected from the group consisting of miR-20, miR-25, miR-191, miR-199a, and miR-199b and a combination thereof.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described herein.

The invention will now be illustrated by the following non-limiting examples.

EXEMPLIFICATION

Methods

Patients and cell samples. Leukemic samples from 158 patients with newly diagnosed AML and 54 samples from patients with AML at relapse(34) or with refractory disease (20) were obtained from the Cell and Tissue Bank at MD Anderson Cancer Center (n=202) and Thomas Jefferson University (n=10), after informed consent was signed according to institutional guidelines (FIG. 4 (Table 1)).

Bone marrow or peripheral blood samples were collected, prepared by Ficoll-Hypaque (Nygaard) gradient centrifugation and cryopreserved. Cytogenetic analyses of the samples were performed at presentation, as previously described[16]. The criteria used to describe a cytogenetic clone and karyotype followed the recommendations of the International System for Human Cytogenetic Nomenclature[17]. An independent set of 36 patients with AML was used to validate miRNAs within the microarray signatures by using qRT-PCR (FIG. 4 (Table 1)). Complete remission (CR) was defined by the presence of < than 5% of blasts in the bone marrow aspirate, absolute peripheral neutrophil count $>1\times10^9$/l and platelets $>100\times10^9$/l.

Peripheral blood mature granulocytes and monocytes, bone marrow CD71+ selected erythrocytes precursors and CD34+ cells from 4 healthy donors, except for CD34+ (10 donors) were purchased from Allcells. In vitro differentiated megakaryocytes were obtained as previously described[18].

RNA Extraction and miRNA Micro Array Experiments.

RNA extraction and miRNA microchip experiments were performed as described in detail elsewhere[19]. Briefly, 5 ug of total RNA from 176 AML patients were hybridized in quadruplicate with probes corresponding to 250 human mature and precursor miRNAs (as described in the miRBase (http://microrna.sanger.ac.uk/) on November 2005)[20].

Real-Time Quantification of microRNAs.

The single tube TaqMan miRNAs as previously described[21] using PCR 9700 Thermocycler ABI Prism 7900HT and the sequence detection system (Applied Biosystems) was selected because it had the least expression variability in the microarray patient data set. Comparative real-time PCR was performed in triplicate, including no-template controls. Relative expression was calculated using the comparative $C_t$ method Data Analysis.

Microarray images were analyzed using GENEPIX PRO. Average values of the replicate spots of each miRNA were background subtracted, log2 transformed, normalized and retained in the expression table when measured as present in at least 10% of the samples. Normalization was performed over a set of housekeeping genes (FIG. 7 (Table 4)) printed onto the chip interspersed through the miRNA probes. In two class comparisons (i.e., CD34 vs. AML) differentially expressed miRNAs were identified by using the test procedure within the Significance Analysis of Microarrays (SAM)[22]. SAM calculates a score for each gene on the basis of the change of expression relative to the standard deviation of all measurements. Since this is a multiple test, permutations are performed to calculate the false discovery rate (FDR) or q-value. MiRNAs with FDRs less than 5% and fold changes more than 2 were considered for further analysis. All data were submitted to the Array Express database with the use of MIAMExpress (accession numbers pending).

Statistical Analysis.

Fisher's exact test, t-Test and chi-square were used to compare baseline characteristics and average miRNA expression between groups of patients. All reported P values were two-sided and obtained using the SPSS software package (SPSS 10.0). Overall survival was calculated from the time of diagnosis until the date of last follow up and e vent-free survival (EFS) from the time of diagnosis until relapse or death. Data were censored for patients who were alive at the time of last follow up. To perform the survival and generate a Kaplan-Meier (KM) plot, miRNA levels measured on the chips and by qRT-PCR were converted into discrete variables by splitting the samples in two classes (high and low expression, according to the median expression in the full set of samples). Survival curves were obtained for each group and compared by using the log-rank test. Hazard Ratios with their 95% confident intervals obtained from the KM method are also reported.

Target Prediction and Microarray Validation

Data validation. To validate the microarray data we used Pearson correlation and linear regression analysis (SPSS software) using 42 miRNA measurements in 10 patients. These functions examine each pair of measurements (one from the chip and the other from RT-PCR ) to determine whether the two variables tend to move together, that is whether the large r values from the chip (high expression) are associated with the lower values from the qRT-PCR (delta Ct). A negative correlation is expected because the qRT-PCR values (delta Ct) are inversed to the expression levels of miRNAs. Log values for both chip and qRT-PCR miRNA measurements were used.

Target prediction. MicroRNA targets were predicted in silico by using TARGETSCAN[32] (www.genes.mit.edu/targetscan) and PICTAR[33] (www.pictar.bio.nyu.edu); both databases predict conserved 3'UTR miRNA targets.

Results

AML Patients Reveal a Distinct Spectrum of miRNA Expression with Respect to Normal CD34+ Progenitor Cells.

Figure 1B:
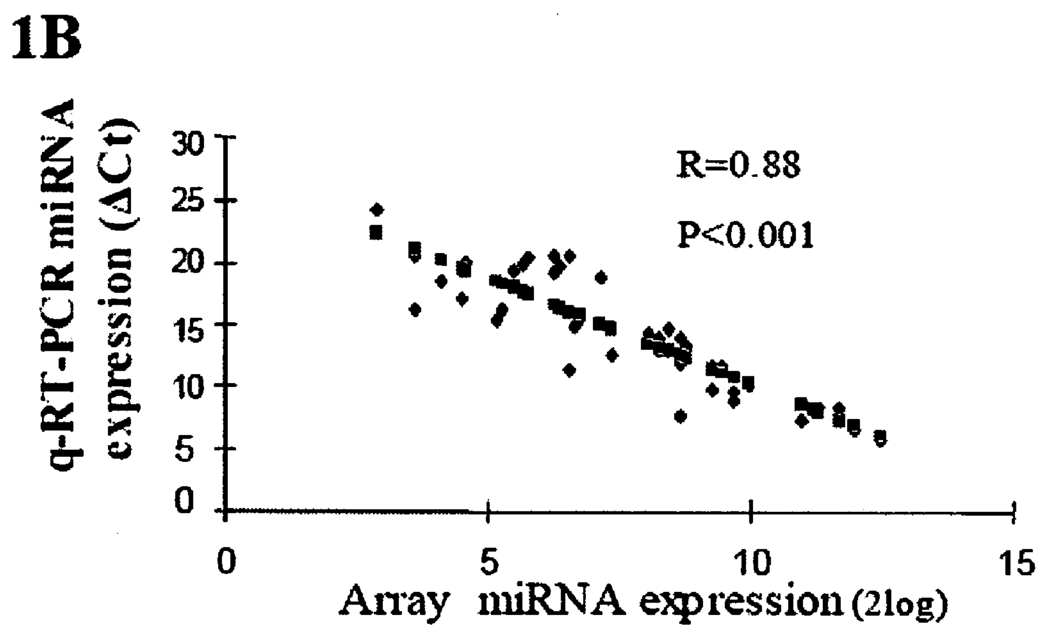

As a first step to wards understanding the possible involvement of miRNAs in the pathogenesis of AML, we analyzed the miRNA expression in 122 newly diagnosed AML patient samples and CD34+ cells from 10 different donors using a miRNA microarray platform[19] (Clinical data in FIG. 4 (Table 1)). SAM identified only down-regulated miRNAs in AML samples compared with CD34+ cells (Table S 2, supporting information). We confirmed many of these differentially expressed miRNAs by using qRT-PCR (FIG. 1A). Additionally, to validate the microarray platform we performed qRT-PCR for miRNAs that were highly, intermediate and low expressed on the chip. As shown in FIG. 1B the miRNA levels measured by either the microarray or the qRT-PCR were very concordant and there was a highly significant correlation between the measures in the two platforms ($r=0.88$, $p<0.001$).

Figure 1C:
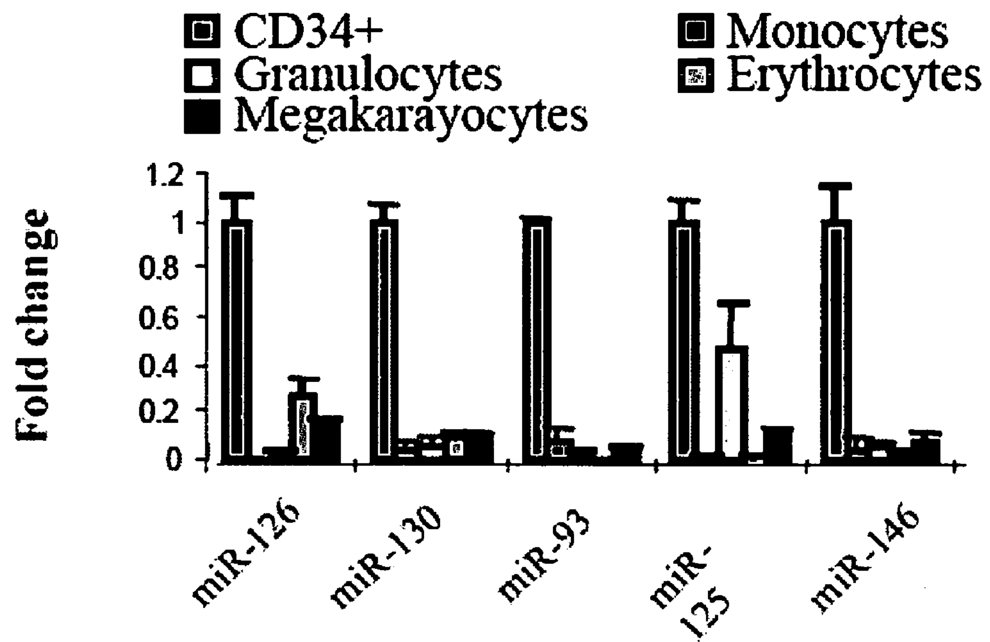
Figure 1D:
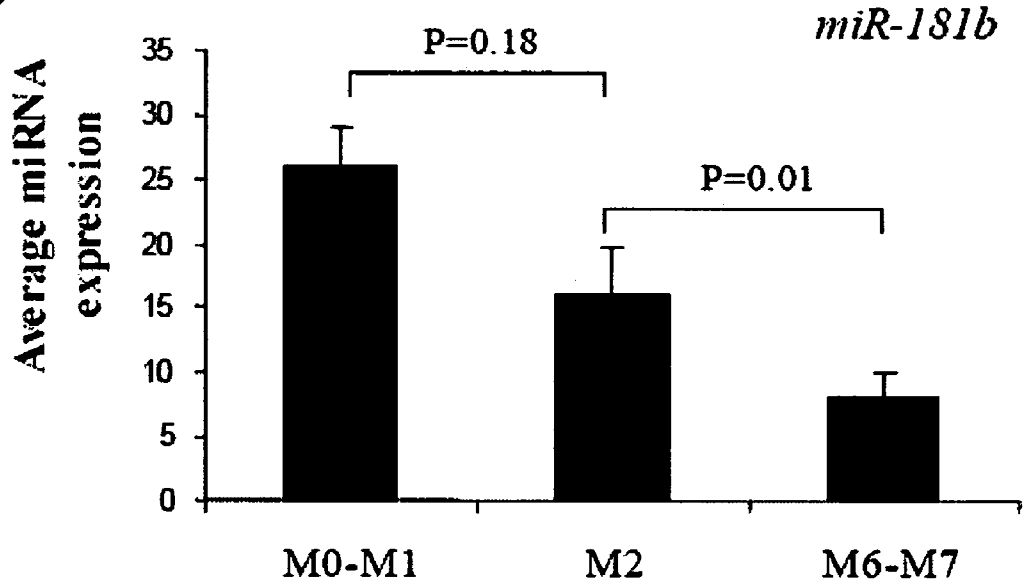
Figure 3A:
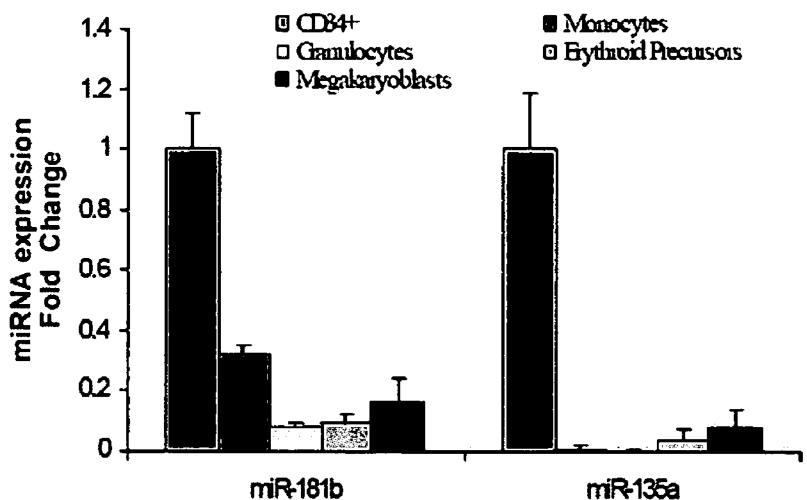
FIG. 3A. Average qRT-PCR of miR-181b and miR-135a expression in bone marrow erythrocytic/megakaryocytic precursors and peripheral blood mature granulocytes/monocytes obtained from four different healthy donors. Results are shown as the fold change in the miRNA expression in the different lineages with respect to that of miR-181b and miR-135b in four CD34+ cells.

A miRNA Signature Correlates with Hematopoietic Differentiation and FAB Classification MiRNA expression has been shown to be informative of the hematopoietic developmental lineage and differentiation stage of tumors[11]. As different profiles characterize normal vs. malignant cells in AML patients, we determine d by qRT-PCR the expression pattern of the most differentially expressed miRNAs between AML samples and CD34+ cells among a panel of human hematopoietic cells, including mature granulocyte s and monocyte s, as well as erythrocyte and megakaryocyte precursors. Many miRNAs down-regulated in AML were also down-regulated in mature and precursor hematopoietic cells (FIGS. 1C and 3A). Two recent studies have described widespread miRNA down-regulation during in vitro differentiation of CD34+ cells to several lineages[18,23]. These results suggest that a subset of miRNAs in leukemia follow closely the differentiation patterns of miRNA expression in normal hematopoiesis. If miRNAs reflect the stage of cell differentiation in leukemia patients, they should also correlate with the French-American and British (FAB) classification of AML[24], which is based on cytomorphology and immunophenotype, both closely associated with the differentiation stage of the leukemia. Indeed, we identified signatures associated with FAB classification. (FIGS. 9-12, Tables 6-9). Within the FAB M0-M1 signature, we identified several miR-181 family members, as well as other miRNAs highly expressed in CD34+ cells, suggesting an expression profile closer to that of stem cells (FIG. 9 (Table 6)). The expression of miR-181b is in fact down-regulated in mature and committed precursors hematopoietic cells from all lineages (FIG. 3A) and similar results were observed in the most differentiated leukemias like FAB M6-M7 (FIG. 1D).

MiRNAs Positively Correlated with White Blood Cell and Blasts Counts

We then investigated whether miRNAs are associated with pretreatment patient characteristics such as age, sex, white blood cell (WBC) count, bone marrow or peripheral blood blasts percentage. We detected a positive correlation in several miRNAs, including miR-155, miR-30b, miR-30c, miR-25 and miR-181b with WBC count, peripheral blood and marrow blast percentage (FIG. 13 (Table 10)).

MicroRNA Signatures Associated with Defined Cytogenetic Subgroups.

To identify miRNA s associated with known cytogenetic abnormalities in AML we studied 116 AML samples with at least 20 metaphases analyzed by conventional karyotype by using permutation adjusted t-tests within SAM. These data are summarized in FIG. 5 (Table 2).

AML with Normal Karyotype.

Figure 1E:
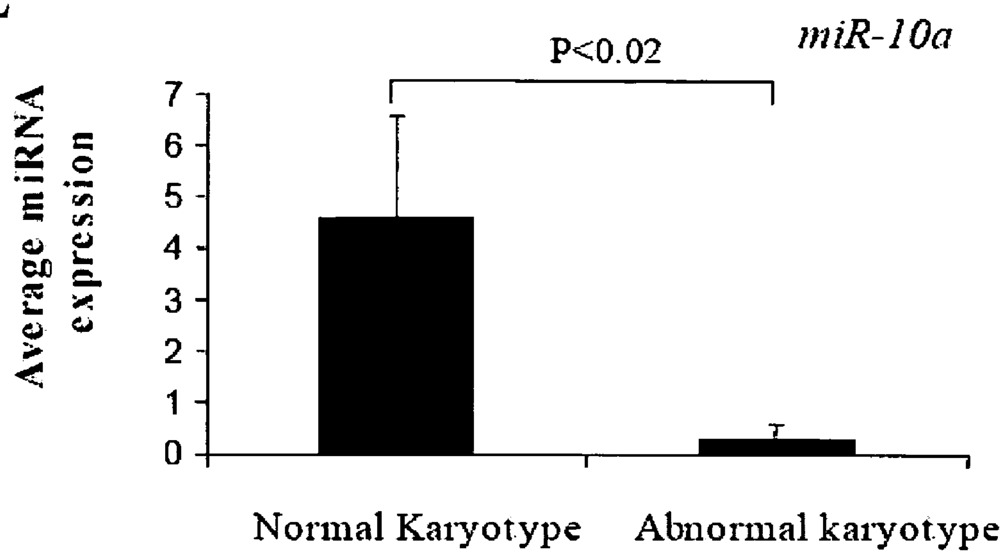
Figure 3B:
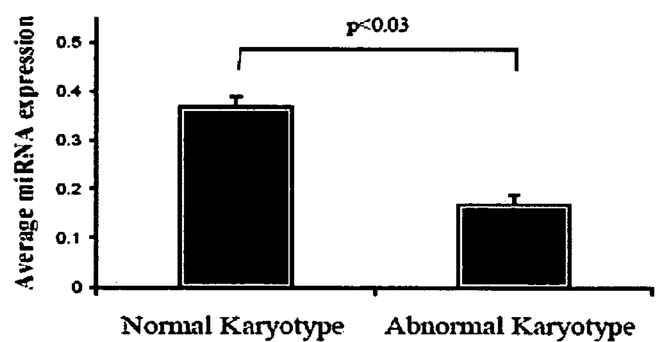
FIG. 3B. Average qRT-PCR expression values of miR-30c in 10 patients with normal karyotype and in 22 patients with abnormal karyotype. The miRNA expression values from the two groups (Normal vs. abnormal karyotype) were compared using t-Test (SPSS).

We identified a signature distinguishing AML cases with a normal karyotype from all other cases of AML with abnormal karyotype (FIG. 14 (Table 11), FIG. 3B). Among the up-regulated genes, miR are located within the cluster of HOX genes, which have been shown to be over expressed in AML with a normal karyotype 6 (FIG. 1E, FIG. 5 (Table 2)). In particular, we and others have shown that Hox embedded miRNAs like miR-10a and miR-196b target several Hox genes, revealing a complex layer of regulation for this family of transcription factors[18,25].

Two previous studies identified high levels of expression of the DNA methyl transferase genes DNMT3A and 3B in normal karyotype AML samples suggesting a potential role for abnormal methylation in the pathogenesis of this subtype[5-6]. Intriguingly, among the down-regulated miRNAs in the normal karyotype group, are present two miRNAs (miR-200c and miR-182), predicted to target DNMT3A and miR-, which is proposed to target DNMT3B. Thus, the down-regulation of these miRNAs may contribute to the over expression of both DNMT3 genes in normal karyotype AML cells.

11q23 Abnormalities

Figure 1F:
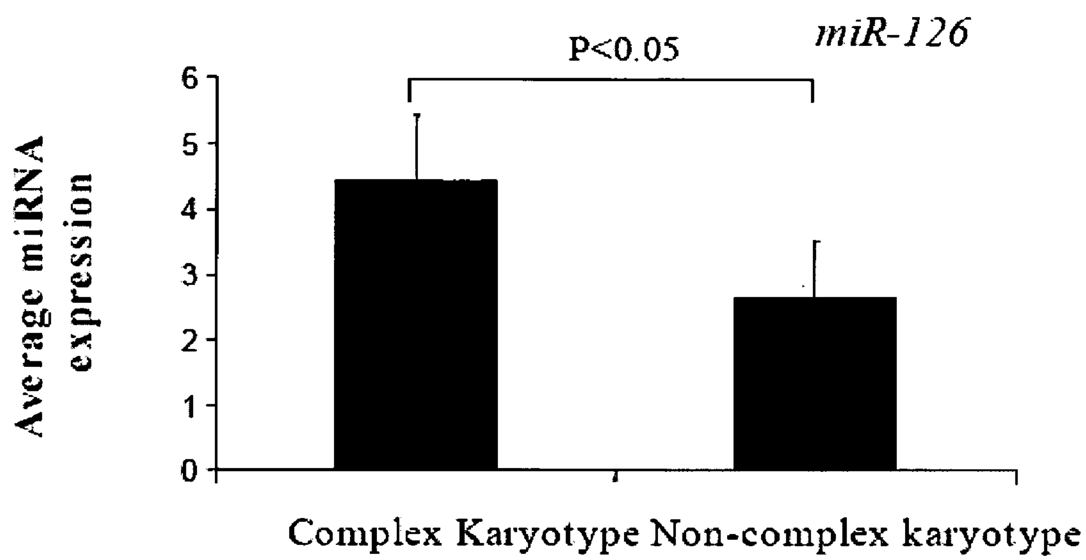

Among the genes down-regulated in patients with t(9;11) [5] and t(6;11)[4] (FIG. 15 (Table 12)), many are predicted to target Hox genes which have been described over-expressed and associated with poor prognosis in this group of patients, i.e., HOXA9 (let7f), HOSA10 (iR-15a), PBX3(let07f, miR-15a and miR-196b) and MEISI (miR-331)[6] (FIG. 15 (Table 12)). Likewise, members of the miR-29 family, also down-regulated in this group, are predicted to target the anti-apoptotic MCLI gene Complex Karyotype Samples with 3 or more cytogenetics abnormalities share a common signature that includes miR-126, miR-26a, miR-34b, miR-30c and miR-301 as the most discriminative genes for this group. (FIG. 16 (Table 13)). Likewise in patients with isolated loss of the chromosome 7, miR-126 was up-regulated (Table S11). Interestingly this miRNA is highly expressed in CD34+ stem cells and down-regulated in other AMLs, except in those with complex karyotype. These results were confirmed in an independent set of AML patients with complex (N=6) and non-complex cytogenetic abnormalities (N=22) by using qRT-PCR (FIG. 1F).

Trisomy 8

The signature obtained using SAM identified many up-regulated miRNAs in patient samples with isolated trisomy 8 (FIG. 18 (Table 15)). Among the up-regulated miRNAs, miR124a and miR-30d are located at 8p21 and 8q23 respectively, suggesting that a gene dosage effect may play a role in the up-regulation of these miRNAs.

MicroRNAs Expression in Relapsed AML Patients

We further investigated miRNAs expression profiles of 54 patients with relapsed acute myeloid leukemia by using our miRNA platform (FIG. 19 (Table 16)). We did not find strong differences between new and treated patients, as reflected by non-significant statistical scores and fold change s lower than 2 (data not shown). However, we observed in these patients FAB and cytogenetics signatures highly similar to those of the new patients (FIGS. 8-17; Tables 5-14), thus confirming the previously described findings. These data suggest that miRNAs expression is largely driven by the differentiation stage of the leukemia and cytogenetics.

MicroRNAs Associated with the Outcome

Figure 2A:
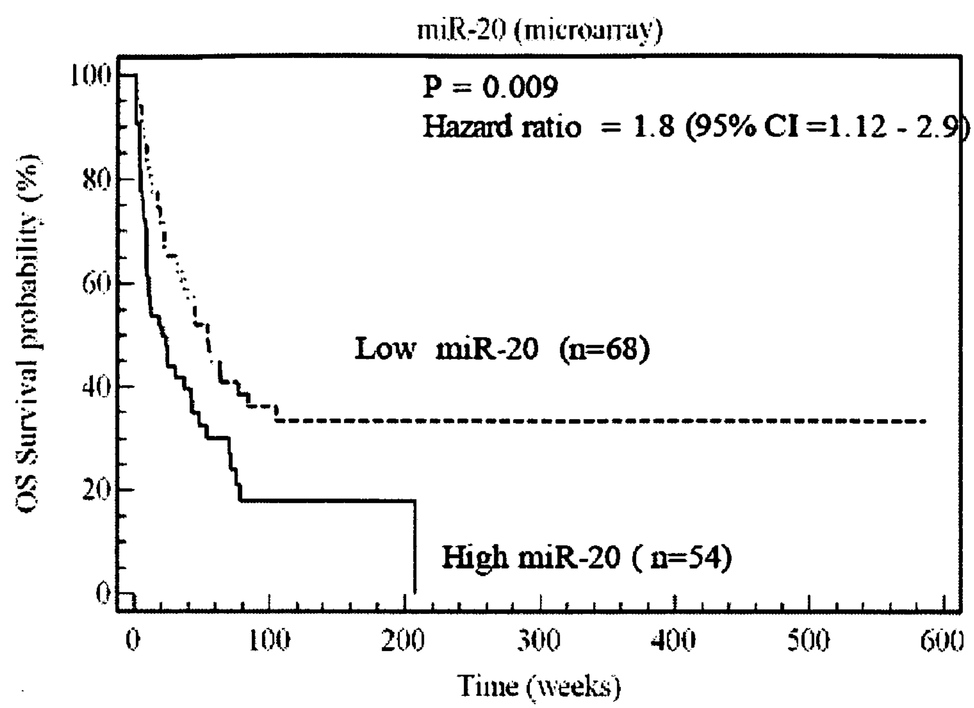
FIGS. 2A-D. MicroRNAs associated with overall survival in newly diagnosed patients with AML. Kaplan-Meier estimates of overall survival for 122 AML patients with high or low expression of miR-20 (FIG. 2A) and miR-25 (FIG. 2B) detected by microarrays. The log-rank test was used to compare differences between survival curves. An independent set of 36 AML patients with similar clinical characteristics (FIG. 4 (Table 1)) was used to validate the outcome predictive power of miR-20 and miR-25 by using a different technology (miRNA qRT-PCR). Kaplan-Meier estimates of overall survival for the 36 AML patients with high or low expression of miR-20 (FIG. 2C) and miR-25 (FIG. 2D) detected by qRT-PCR are shown. Hazard ratios with 95% confidence intervals (CI 95%) were obtained by the Kaplan-Meier method.
Figure 2B:
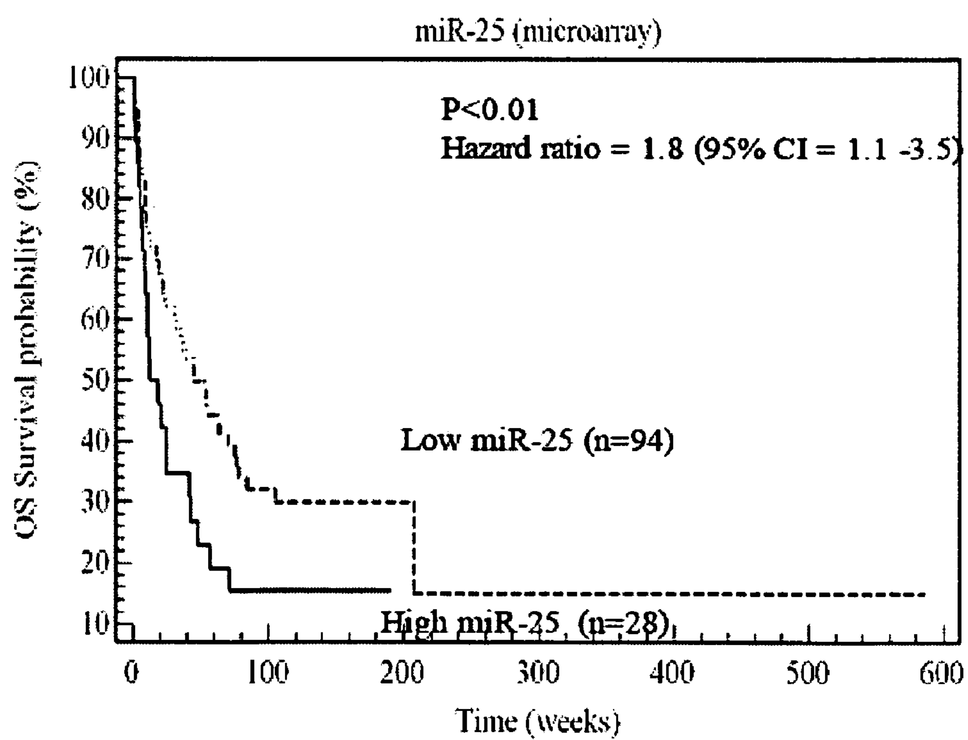
Figure 2C:
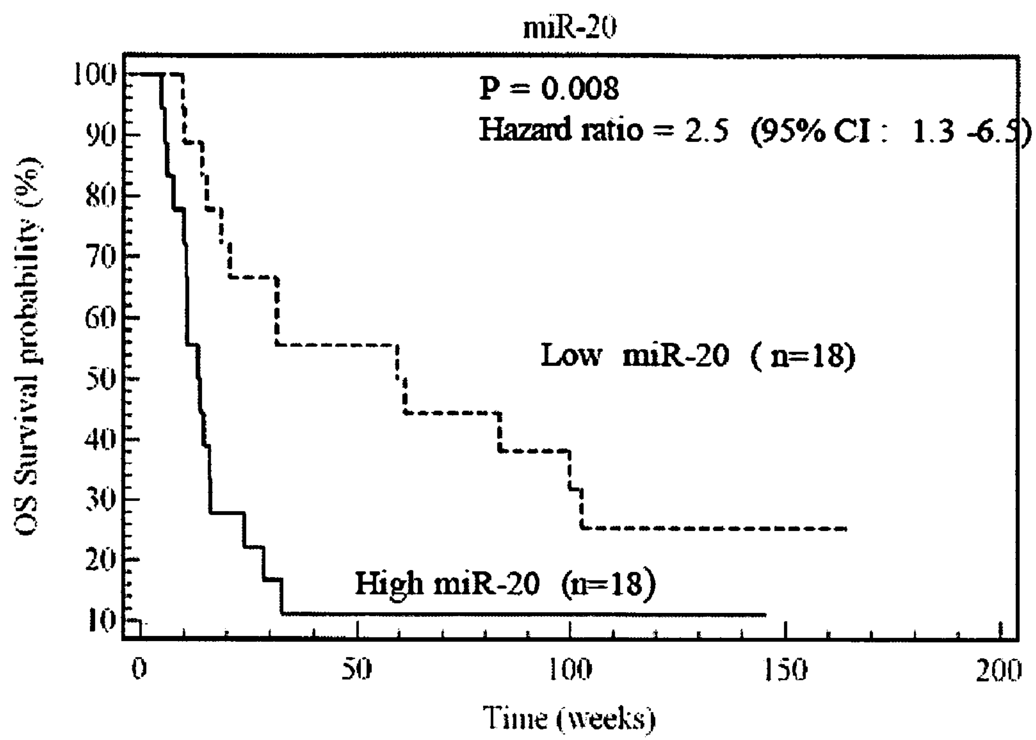
Figure 2D:
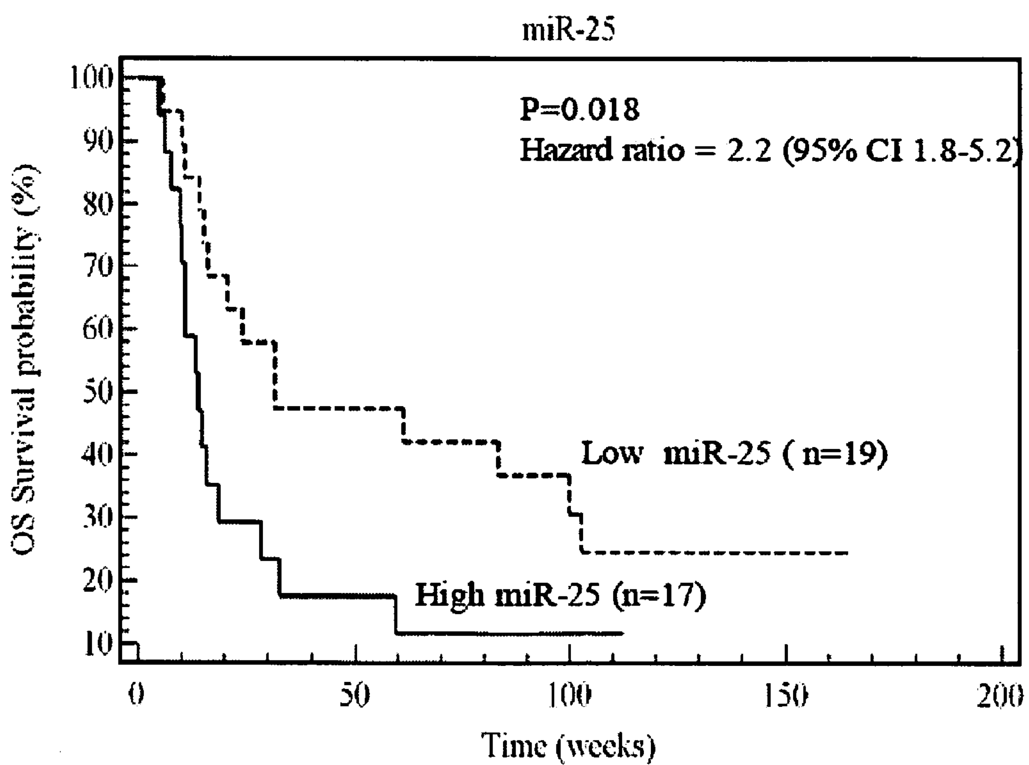

We identified a small number of miRNAs with a false discovery rate lower than 1% and a SAM survival score (Cox regression) higher than 2 associated with overall survival in 122 newly diagnosed AML patients. All the identified genes: miR-17-5p, MIR-20, miR-miR-182, miR-191, miR-199a and miR-199b when over-expressed, adversely affected overall survival (FIG. 6 (Table 3)). We then estimated the survival probabilities of the 122 AML patients with high or low expression of the above miRNAs by using Kaplan-Meier method and log-rank test for survival curves comparisons. We confirmed the SAM results for miR-20 (FIG. 2A), miR-25 (FIG. 2B), miR-191, miR-199a and miR-199b, except for miR-17-5p and miR-182(p=0.06) [Data not shown]. To assess whether and by using qRT-PCR in an independent sample of 36 patients with AML, we measured miR-20 and miR-25 by using qRT-PCR in an independent sample of 36 patients with AML.

Patients with high expression of miR-20 or miR-25 were found to have significant shorter overall survival (OS) (FIGS. 2A and 2B) and event-free survival (miR-20 p=0.012, HR=2.39 CI 95%:1.3-5.2 and miR-25 p=0.018, HR=2.23 CI 95%:1.7-4.9) than AML patients with low expression. None of the other clinical characteristics, including sex, age, unfavorable cytogenetics, white blood cells and peripheral blasts counts were significantly associated with survival in this independent set of 36 AML patients (data not shown).

MiRNAs Associated with Failure to Achieve Remission with Induction Treatment

Figure 3C:
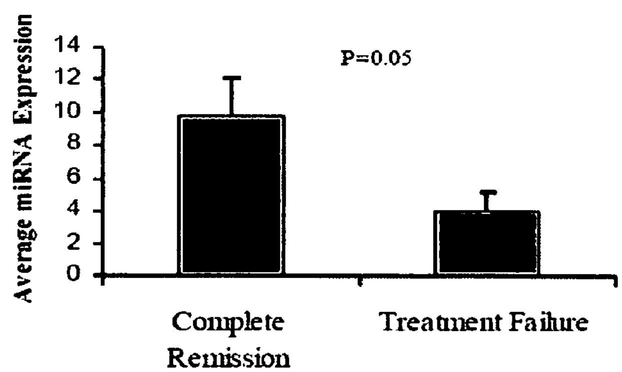
FIG. 3C. Average miR-29b expression in AML patients who received induction chemotherapy with idarubicin and cytarabine by qRT-PCR in 12 independent patients with newly diagnosed AML that achieve complete remission (6) or have failure to achieve induction chemotherapy (6). The miRNA expression values from the two groups (CR vs. failure) were compared using t-Test (SPSS).

As we had shown that biological and genetic findings in AML patients correlated with expression of different miRNAs, we then further investigated the relation between treatment response and miRNA expression. To identify miRNAs associated with induction treatment response, we analyzed the expression of miRNAs in a group of 24 AML patients at diagnosis, all treated with idarubicin 12 mg/m2 daily on days 1 to 3 and cytarabine 1500 mg/m2 continuous infusion for 4 days (FIG. 20 (Table 17)). SAM identified 25 miRNAs down-regulated at diagnosis in patients who had treatment failure (FIG. 21 (Table 18)). Among them, miR-29b and miR-29c are predicted to target MCLI, a gene associated with resistance to a variety of chemotherapeutic agents[26]. To confirm these results, we measured miR-29b by qRT-PCR in an independent set of AML patients with similar baseline characteristics but treated with various chemotherapy protocols. We found that miR-29b is down-regulated in patients with treatment induction failure compared with patients who achieve complete re mission (FIG. 3C).

Discussion

In this study we used a microarray platform to perform genome wide miRNome analysis of AML samples and their progenitor CD34+cells. Despite the fact that some miRNAs were up-regulated in AML patients compared with CD34+ cells, most of the miRNAs were down-regulated. Some of the down-regulated miRNAs include markers for the differentiation stage of the leukemia that correlate well with the FAB classification of AML. Lu et al. reported that miRNAs reflect the developmental lineage and differentiation state of tumors[11]. Whether the miRNA subsets identified here are only markers for the differentiation stage or some of these miRNAs have a pathogenic role remains to be elucidated.

Using SAM, we identified molecular signatures associated with several cytogenetic group s. Among the strongest signatures were those associated to 11q23 rearrangements, normal karyotype and trisomy 8.

A Subset of miRNAs Acts as Oncogenic miRNAs.

The up-regulated cluster spanning miR-17 and miR-20, target E2FI[27], thus impacting over the cell cycle regulation. In contrast, members of the miR-29 family, down-modulated in AML and associated with failure to achieve remission, is predicted to target MCLI, a critical apoptosis regulator, found up-regulated in cells that are resistant to a variety of chemotherapeutic agents[26]. Moreover other members of this family have been identified in the signature associated with short event-free survival in CLL patients 28 and in AML cancer 29, indicating that this miRNA could be a tumor suppressor non-coding gene.

We describe molecular signatures associated with overall and event-free survival (OS). Several observations strengthen our results. First, we identified miRNAs associated with survival despite the overall poor prognosis and short survival of the patients studied where outcome differences would be difficult to demonstrate. Second, two of the miRNAs associated with survival (miR-20 and miR-25) were also correlated with high WBC and blast counts, all features closely relate d with survival. Third, we identified several up-regulated miRNAs in common with the shared signatures of six solid cancers (such as miR-17, miR-20 and miR-191)[10] some of them (like miR-17 and miR-20) with well characterized roles in oncogenesis[27-30].

In summary, we demonstrate s that a subset of miRNAs are markers for the differentiation stage of the leukemia and correlate with the FAB classification, while others are clearly deregulated in AML, associate d with cytogenetic groups and outcome. Finally, we show that miRNAs may be involved in leukemogenesis acting as oncogenes and tumor suppressors.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

All scientific and patent publications referenced herein are hereby-incorporated by reference. The invention having now been described by way of written description and example, those of skill in the art will recognize that the invention can be practiced in a variety of embodiments, that the foregoing description and example is for purposes of illustration and not limitation of the following claims.

The relevant teachings of all publications cited herein that have not explicitly been incorporated by reference, are incorporated herein by reference in their entirety. While this invention has been particularly shown and described with references to preferred embodiments thereof, it will be understood by those skilled in-the art that various changes in form and details may be made therein without departing from the scope of the invention encompassed by the appended claims.

REFERENCES

1. Lowenberg B, Downing J. R., Burnett A. Acute Myeloid leukemia. *N Engl J Med* 1999; 341: 1051-1062.

2. Grimwade D, Haferlach T. Gene expression profiling in acute myeloid leukemia. *N Engl J Med* 2004; 350:1676-7.

3. Burnett A K. Current controversies: which patients with acute myeloid leukemia should receive bone marrow transplantation? An adult theater's view. *Br. J Haematol* 2002; 118:357-64.

4. Drobyski W R. The role of allogeneic transplantation in high-risk acute myeloid leukemia. *Leukemia* 2004; 10: 1565-8.

5. Bullinger L, Dohner K, Bair E, et al. Use of gene-expression profiling to identify prognostic subclasses in adult acute myeloid leukemia. *N Eng J Med* 2004; 350:1605-1616.

6. Valk P J M, Verhaak G W, Beijen M A. Prognostically useful gene-expression profiles in acute myeloid leukemia. *N Eng J Med* 2004, 350:1617-1628.

7. Pasquinelli A E, Hunter S, Bracht J. MicroRNAs: a developing story. *Curr O, Genet Dev* 2005; 15: 200-5.

8. Bartel D. MicroRNAs: genomics, Biogenesis, Mechanism, and Function. *Cell* 2004; 116:281-297.

9. Chen C Z, Li L, Lodish H, Bartel D. MicroRNAs Modulate Hematopoietic lineage Differentiation. *Science* 2004; 303:83-86.

10. Volinia S, Calin G, Liu C G, et al. A microRNA expression signature in human solid tumors defines cancer targets. *Proc Nad Acad Sci USA* 2006; 103: 2257-61.

11. Lu J, Getz G, Miska E A, et al. MicroRNA expression profiles classify human cancers. *Nature* 2005; June 9; 435: 834-8.

12. Calin G A, Liu C G, Sevignani C, et al. MicroRNA profiling reveals distinct signatures in B-Cell Chronic Lymphocytic leukemias. *Proc Nad Acad Sci USA* 2004; 101: 1175560.

13. Eis P S, Tam W, Sun, L. Accumulation of miR-155 and BIC RNA in human B cell lymphomas. *Proc Nad Acad Sci USA* 2005; 102: 3627-32.

14. Metzler M, Wilda M, Busch K, et al. High expression of miR-155/BIC RNA in children with Burkitt lymphoma. *Genes Chomosomes and Cancer* 2004; 39:167-9.

15. Costinean, S. et al. Pre B cell proliferation and lymphoblastic leukemia/high grade lymphoma in Eμ miR155 transgenic mice. *Proc Nad Acad Sci USA* 2006; 103: 7024-9.

16. Bloomfield C D. Prognostic factors for selecting curative therapy for adult acute myeloid leukemia. *Leukemia* 1992; 6:65-67. 21.

17. An International System for Human Cytogenetic Nomenclature (1985) ISCN 1985. Report of the Standing Committee on Human Cytogenetic Nomenclature. *Bi Orig Artic Ser* 1985; 21:1-117.

18. Garzon R, Pichiorri F, Palumbo T, et al. MicroRNAs fingerprints during human megakaryocytopoiesis. *Proc Nad Acad Sci USA* 2006; 103: 5078-83.

19. Liu C G, Calin G A, Meloon B, et al. An oligonucleotide microchip for genomic-wide microRNA profiling in human and mouse tissues. *Proc Nad Acad Sci USA* 2004; 101: 11755-60.

20. Griffiths-Jones S. The microRNA registry. *Nucleic Acids Res* 2004; 32, Database issue D109-D111.

21. Chen C, Ridzon D A, Broomer A J, et al. Real-Time quantification of microRNAs by stem-loop RT-PCR. *Nucleic Acids Res* 2005:33:e179.

22. Tusher V G, Tibshirani R, Chu G. Significant analysis of microarrays applied to the ionizing radiation response. *Proc Natl Acad Sci USA* 2001; 98:5116:21.

23. Felli N. Pelosi E, Beta R, et al. Lineage-Specific Expression and functional Relevance of MicroRNA genes in Normal Hematopoiesis. *Blood* (ASH national meetings abstract) 2006; 106: 2263.

24. French-American-British (FAB) Cooperative Group. Proposed revised criteria for the classification of acute myeloid leukemia. *Ann Intern Med.* 1985; 103:620-685.

25. Yekta S, Shih I H, Bartel D P. Micro-RNA direct cleavage of HOXB8 mRNA. *Science* 2004; 304:594-6.

26. Zhou P, Qian L, Kozopas K M, Craig R W: Mcl-1, a Bcl-2 family member, delays the death of hematopoietic cells under a variety of apoptosis-inducing conditions. Blood 1997; 89:630.

27. O'Donnell K A, Wentzel E A, Zeller K I, Dang C V, Mendell J T. C-myc regulated microRNAs modulate E2F1 expression. *Nature* 2005; 435:839-43.

28. Calin G A, Terracing M, Camino A, et al. A MicroRNA signature associated with prognosis and progression in chronic lymphocytic leukemia. *N Engl J Med.* 2005; 353: 1793-801.

29. Yanaihara N, Caplen N, Bowman, E, et al. Unique microRNA molecular profiles in AML cancer diagnosis and prognosis. *Cancer Cell* 2006; 9:189-98.

30. He L, Thomson J M, Hemann M T. A microRNA polycistron as a potential oncogene. re 2005: 435: 828-33.

31. Lewis B P, Shih I H, Jones-Rhoades M W, Bartel P, Burge C B. Prediction of mammalian microRNA targets. *Cell* 2003; 115:787-798.32. Krek A, Grün D, Poy M, et al. Combinatorial microRNA target *Nature G* 37: 495-500.

32. Lewis B P, Burge C B, Bartel D. Conserved seed pairing often flanked by adenosines, indicates that thousands of human genes are microRNA targets. *Cell* 2005; 120:15-20.

33. Krek A, Grun D, Poy M N, et al. Combinatorial microRNA target predictions. *Nat Genet.* 2005; 37: 495-500.

What is claimed is:

1. A method of determining survival prognosis in a subject with AML, comprising:

measuring the level of at least one miR-20 gene product in a test sample from a subject with AML, and determining the subject's survival prognosis, wherein if the level of the miR-20 gene product in the test sample is higher relative to the level of a corresponding miR-20 gene product in a control sample, the subject is determined to have a shorter overall survival prognosis.

2. The method of claim 1, which further comprises measuring the level of a miR selected from the group consisting of: miR-25, miR-191, miR-199a, and miR-199b and combinations thereof.

3. The method of claim 2, wherein the level of the at least one miR gene product in the test sample is less than the level of the corresponding miR gene product in the control sample.

4. The method of claim 2, wherein the level of the at least one miR gene product in the test sample is greater than the level of the corresponding miR gene product in the control sample.

5. A method of determining the prognosis of a subject with acute myeloid leukemia, comprising measuring the level of at least one miR-20 gene product in a test sample from said subject, wherein:

the miR-20 gene product is associated with an adverse prognosis in AML; and an increase in the level of the at least one miR-20 gene product in the test sample, relative to the level of a corresponding miR-20 gene product in a control sample, is indicative of an adverse prognosis.

6. A method of diagnosing whether a subject has, or is at risk for developing, shorter overall survival-type AML, comprising:

(1) reverse transcribing miR-20 RNA from a test sample obtained from the subject to provide a set of target oligodeoxynucleotides;

(2) hybridizing the target oligodeoxynucleotides to a microarray comprising miR-20miRNA-specific probe oligonucleotides to provide a hybridization profile for the test sample; and (3) comparing the test sample hybridization profile to a hybridization profile generated from a control sample, wherein an increase in the signal of at least one miR-20 miRNA is indicative of the subject either having, or being at risk for developing, shorter overall survival-type AML.

7. A method of diagnosing whether a subject has, or is at risk for developing, AML with an adverse prognosis in a subject, comprising:

(1) reverse transcribing miR-20 RNA from a test sample obtained from the subject to provide a set of target oligodeoxynucleotides;

(2) hybridizing the target oligodeoxynucleotides to a microarray comprising miR-20 miRNA-specific probe oligonucleotides to provide a hybridization profile for said test sample; and (3) comparing the test sample hybridization profile to a hybridization profile generated from a control sample, wherein an increase in the signal is indicative of the subject either having, or being at risk for developing, AML with an adverse prognosis.

* * * * *

UNITED STATES PATENT AND TRADEMARK OFFICE

CERTIFICATE OF CORRECTION

PATENT NO. : 8,034,560 B2
APPLICATION NO. : 12/523915
DATED : October 11, 2011
INVENTOR(S) : Carlo M. Croce It is certified that error appears in the above-identified patent and that said Letters Patent is hereby corrected as shown below:

In the Specification

Column 1, Line 5 add Government Support Clause:
--This invention was made with government support under grant numbers CA076259, CA016058, and CA081534 awarded by the National Institutes of Health. The government has certain rights in the invention.--

Signed and Sealed this
Fourth Day of August, 2020

Andrei Iancu
*Director of the United States Patent and Trademark Office*